United States Patent
Stark et al.

(10) Patent No.: US 6,820,979 B1
(45) Date of Patent: *Nov. 23, 2004

(54) PUPILOMETER WITH PUPIL IRREGULARITY DETECTION, PUPIL TRACKING, AND PUPIL RESPONSE DETECTION CAPABILITY, GLAUCOMA SCREENING CAPABILITY, INTRACRANIAL PRESSURE DETECTION CAPABILITY, AND OCULAR ABERRATION MEASUREMENT CAPABILITY

(75) Inventors: Lawrence W. Stark, Berkeley, CA (US); Claudio M. Privitera, Berkeley, CA (US); Kamran Siminou, Newport Beach, CA (US); Jeffrey Oliver, Cedar Park, TX (US)

(73) Assignee: Neuroptics, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/711,675

(22) Filed: Nov. 9, 2000

Related U.S. Application Data

(63) Continuation-in-part of application No. 09/523,778, filed on Mar. 13, 2000, now Pat. No. 6,260,968, which is a continuation of application No. 09/298,670, filed on Apr. 23, 1999, now Pat. No. 6,116,736.

(51) Int. Cl.⁷ .................................................. A61B 3/14
(52) U.S. Cl. ..................................................... 351/206
(58) Field of Search ............................... 351/204, 205, 351/206, 209, 210, 211, 212, 221, 246; 600/398, 474, 549, 399, 400; 382/117

(56) References Cited

U.S. PATENT DOCUMENTS

| | | |
|---|---|---|
| 3,533,683 A | 10/1970 | Stark et al. ........... 351/1 |
| 3,533,684 A | 10/1970 | Stark et al. ........... 351/1 |
| 3,638,740 A | 2/1972 | Shaw .................. 128/2 |
| RE28,873 E | 6/1976 | Morgan ............... 128/249 |
| 3,966,310 A | 6/1976 | Larson ................ 351/16 |
| 4,157,864 A | 6/1979 | Koller et al. ......... 351/160 |
| 4,194,815 A | 3/1980 | Trombley ............. 351/160 |
| 4,410,245 A | 10/1983 | Koester ............... 351/219 |
| 4,485,820 A | 12/1984 | Flower ................ 128/633 |
| 4,641,349 A * | 2/1987 | Flom et al. .......... 382/117 |
| 4,649,908 A | 3/1987 | Ghaly ................. 128/132 |
| 4,652,099 A | 3/1987 | Lichtman ............. 351/162 |
| 4,664,490 A | 5/1987 | Rol ..................... 351/219 |
| 4,755,043 A | 7/1988 | Carter ................. 351/205 |

(List continued on next page.)

FOREIGN PATENT DOCUMENTS

DE    949084    9/1956

OTHER PUBLICATIONS

L. Stark, et al., *Pupil Unrest: An Example of Noise in a Biological Servomechanism*, Nature, 4639, pp. 857–858, Sep. 27, 1958.

(List continued on next page.)

*Primary Examiner*—George Manuel
(74) *Attorney, Agent, or Firm*—Mikael Havluciyan

(57) ABSTRACT

A pupilometer having a pupil irregularity or non-uniformity detection capability. The pupilometer may comprise an imaging sensor for generating signals representative of a pupil of an eye, a data processor; and a program executable by the data processor for enabling the data processor to process signals received from the imaging sensor and to thereby identify one or more regions of non-uniformity within an image of a perimeter of the pupil. The pupilometer may incorporate several innovative calibration and thresholding routines and may provide the basis for an innovative medical diagnostics system, when coupled to a network containing a suitable medical database and data processing hardware.

197 Claims, 13 Drawing Sheets

U.S. PATENT DOCUMENTS

| | | | |
|---|---|---|---|
| 4,863,260 A | 9/1989 | Gersten et al. | 351/212 |
| 4,871,247 A | 10/1989 | Haynes | 351/219 |
| 4,907,597 A | 3/1990 | Chamoun | 128/731 |
| 4,907,872 A | 3/1990 | Schirmer et al. | 351/160 |
| 4,966,452 A | 10/1990 | Shields et al. | 351/219 |
| 5,010,891 A | 4/1991 | Chamoun | 128/731 |
| 5,117,835 A | 6/1992 | Mick | 128/748 |
| 5,137,345 A | 8/1992 | Waldorf et al. | 351/206 |
| 5,139,326 A | 8/1992 | Snider | 351/205 |
| 5,179,953 A | 1/1993 | Kursar | 128/645 |
| 5,187,506 A | 2/1993 | Carter | 351/221 |
| 5,204,703 A | 4/1993 | Hutchinson et al. | 351/210 |
| 5,214,456 A | 5/1993 | Gersten | 352/212 |
| 5,231,674 A | 7/1993 | Cleveland et al. | 382/2 |
| 5,291,560 A | 3/1994 | Daugman | 382/2 |
| 5,297,554 A | 3/1994 | Glynn et al. | 128/665 |
| 5,336,215 A | 8/1994 | Hsueh et al. | 606/4 |
| 5,408,998 A | 4/1995 | Mersch | 128/633 |
| 5,430,505 A | 7/1995 | Katz | 351/208 |
| 5,490,098 A | 2/1996 | Kardon | |
| 5,528,323 A | 6/1996 | Fujieda et al. | 351/218 |
| 5,543,865 A | 8/1996 | Nanjo | 351/206 |
| 5,565,939 A | 10/1996 | Fujieda | 351/212 |
| 5,646,709 A | 7/1997 | Carter | 351/218 |
| 5,661,538 A | 8/1997 | Carter | 351/237 |
| 5,772,298 A | 6/1998 | Miyake | 351/205 |
| 5,784,145 A | 7/1998 | Ghodse et al. | 351/205 |
| 5,813,982 A * | 9/1998 | Baratta | 600/398 |
| 5,883,691 A | 3/1999 | Ishikawa et al. | 351/221 |
| 5,892,568 A | 4/1999 | Carter | 351/221 |
| 5,963,300 A | 10/1999 | Horwitz | 351/209 |
| 6,022,109 A | 2/2000 | Dal Santo | 351/221 |
| 6,115,111 A | 9/2000 | Korah et al. | 356/4.01 |
| 6,199,985 B1 | 3/2001 | Anderson | 351/221 |

OTHER PUBLICATIONS

L. Stark, *Stability, Oscillations, and Noise in the Human Pupil Servomechanism*, Procedings of the IRE, pp. 1925–1939, 1959.

S. Asano, et al., *Pupillometry, Quarterly Progress Report No. 66*, Mass. Inst. of Technology, pp. 404–412, Jul. 15, 1962.

C.A. Finnila, *A Convenient Eye Position and Pupil Size Meter* (partial), 4 pages, 1960.

A. Yarbus, *Eye Movements and Vision*, Plenum Press, N.Y., pp. 28–41, 1967.

Usui, et al., *Sensory and Motor Mechanisms Interact To Control Amplitude of Pupil Noise*, Vision Res., vol. 18, pp. 505–507, 1978.

Marshall, et al., *The Oval Pupil: Clinical Significance and Relationship To Intracranial Hypertension*, J. Neurosurg, vol. 58, pp. 566–568, Apr. 1983.

Sun, et al., *Pupillary Escape Intensified By Large Pupillary Size*, Vision Res., vol. 23, No. 6, pp. 611–615, 1983.

Stark, *The Pupil As A Paradigm For Neurological Control Systems*, IEEE Transactions On Biomedical Engineering, vol. BME–31, No. 12, pp. 919–923, Dec. 1984.

Krenz, et al., *Neurophysiological Model Of The Normal And Abnormal Human Pupil*, IEEE Transactions On Biomedical Engineering, vol. BME–32, No. 10, pp. 817–825, Oct. 1985.

Marshall, et al., *Pupillary Abnormalities, Elevated Intracranial Pressure And Mass Lesion Location, Intracranial Pressure VI*, Springer–Verlag Berlin Heidelberg, pp. 656–660, 1986.

Stark, et al., *Instrumentation And Robotic Processing Using Top–Down Model Control*, Robotics and Manufacturing, ASME Press, 675–682, 1988.

Bishop, *Pathologic Pupillary Signs: Self–Learning Module, Part 1*, Critical Care Nurse, vol. 11, No. 6, pp. 58–63.

Bishop, *Pathologic Pupillary Signs: Self–Learning Module, Part 2*, Critical Care Nurse, vol. 11, No. 7, pp. 58–67.

Bishop, *Pathologic Pupillary Signs: Self–Learning Module, Part 3*, Critical Care Nurse, vol. 11, No. 8, pp. 30–32.

Stark, *The Pupil As A Paradigm Example A Neurological Control System: Mathematical Approaches in Biology, The Pupil: Anatomy, Physiology, and Clinical Applications*, vol. I, Iowa State University Press, pp. 630–647, 1993.

Myers, et al., *Level Dependent Signal Flow In The Light Pupil Reflex*, Biological Cybernetics, 68, 229–234, 1993.

Krieger, et al., *Prognostic And Clinical Relevance Of Pupillary Responses, Intracranial Pressure Monitoring, And Brainstem Auditory Evoked Potentials In Comatose Patients With Acute Supratentorial Mass Lesions*, Critical Care Medicine, vol. 21, No. 12, pp. 1944–1950, Dec. 1993.

Chesnut, et al., *The Localizing Value Of Assymetry In Pupillary Size In Severe Head Injury: Relation To Lesion Type And Location*, Neurosurgery, vol. 34, No. 5, pp. 840–846, May 1994.

Fairville Medical Options, Inc., Pupilscan II, *Hand–Held, Cordless Pupillometer*, 4 pages, Feb. 12, 1997.

Fairville Medical Options, Inc., Pupilscan II, *Hand–Held, Electronic Pupillometer*, 3 pages.

AMTech GmgH, *Introducing CIP: Compact Integrated Pupillograph and Nystagmograph*, 18 pages, 9/97.

ASL Applied Science Laboratories, Pupilscreen, *Pupilscreen Automatic Self Measurement Pupillometry*, 5 pages.

ASL, *Model 1050, Pupilscan & Pupilscreen*, 5 pages, 1997.

Stark, et al., *Top–Down And Bottom–Up Image Processing*, Proceedings of IEEE 1997 International Conference On Neural Networks, 6 pages, Jun. 1997.

Japio (Patent Abstracts of Japan) English Language Abstract for Japanese Patent Application JP 7–171104, "Outer Diameter Measuring Equipment, Electronic Pupil Meter, and Autonomic Function Inspecting Device".

H. J. Wyatt, "The Form of the Human Pupil", *Vision Res.*, vol. 35, No. 14, pp.2021–2036, 1995.

EPO International Search Report, Feb. 27, 1994, EPO Patent Appliation No. 00928240.

* cited by examiner

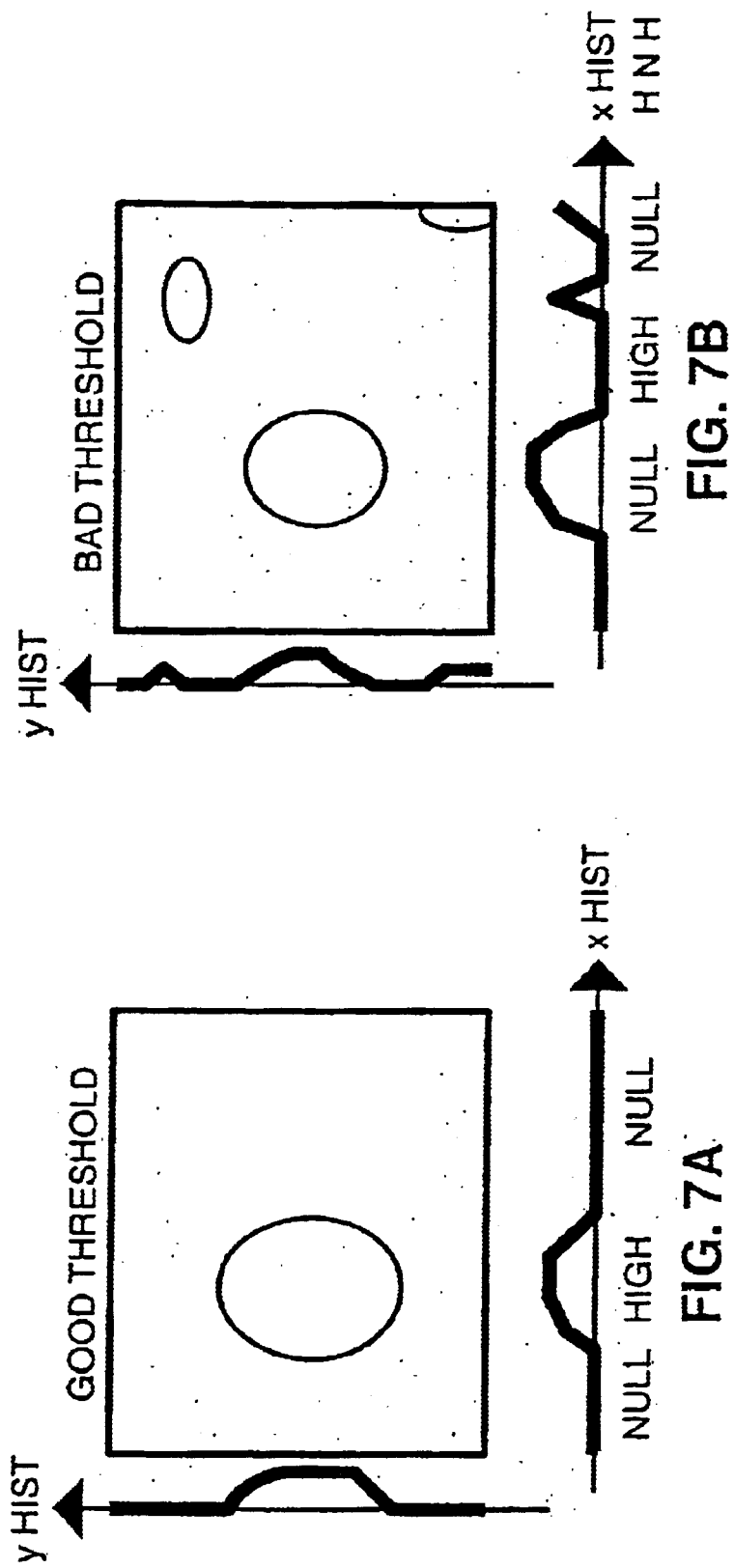

PUPILOMETER WITH PUPIL IRREGULARITY DETECTION, PUPIL TRACKING, AND PUPIL RESPONSE DETECTION CAPABILITY, GLAUCOMA SCREENING CAPABILITY, INTRACRANIAL PRESSURE DETECTION CAPABILITY, AND OCULAR ABERRATION MEASUREMENT CAPABILITY

This is a continuation-in-part of U.S. patent application Ser. No. 09/523,778, filed Mar. 13, 2000 now U.S. Pat. No. 6,260,968, which is a continuation of U.S. patent application Ser. No. 09/298,670, filed Apr. 23, 1999, now U.S. Pat. No. 6,116,736. This further claims priority from International Application No. PCT/US/00/10655, filed Apr. 21, 2000. All of the above mentioned applications are incorporated herein by reference.

FIELD OF THE INVENTION

The present invention relates generally to pupilometry systems and, more particularly, to pupilometry systems having a pupil irregularity detection, pupil tracking, and pupil response detection capability, as well as glaucoma screening capability, corneal topography measurement capability, intracranial pressure detection capability, and ocular aberration measurement capability. In one particularly innovative aspect, the present invention relates to hand-held pupilometry systems having a pupil irregularity detection capability, to methods and processing sequences used within such systems, and to methods of using such systems.

In another innovative aspect, the present invention relates to a medical diagnostics system incorporating a pupilometer and medical database for correlating actual or derived pupilary image analysis data with stored medical data to formulate medical diagnoses, and to methods of implementing and utilizing such a diagnostics system.

In another innovative aspect, the present invention relates to a medical diagnostics system incorporating a pupilometer which can be used to screen for Glaucoma, and for methods of implementing and utilizing such a diagnostics system.

In another innovative aspect, the present invention relates to a medical diagnostics system incorporating a pupilometer for detecting elevated intracranial pressure, and for methods of implementing and utilizing such a diagnostics system.

In another innovative aspect, the present invention relates to a medical diagnostics system incorporating a pupilometer for assessing the level of brain function, and for methods of implementing and utilizing'such a diagnostics system.

In another innovative aspect, the present invention relates to a medical diagnostics system incorporating a pupilometer for testing the functional integrity of afferent peripheral and cranial pathways as well as testing efferent cranial nerve involvement in patients with afferent pupilary defects, and for methods of implementing and utilizing such a diagnostics system.

In another innovative aspect, the present invention relates to a medical diagnostics system incorporating a pupilometer for testing the functional integrity of auditory pathways, and for methods of implementing and utilizing such a diagnostics system.

BACKGROUND OF THE INVENTION

Systems for monitoring pupil size and pupil responsiveness characteristics are well known in the art and are generally referred to as pupilometry systems or, simply, pupilometers. One early pupilometer is described in U.S. Pat. No. 3,533,683, which issued to Stark et al. on Oct. 13, 1970 and is entitled "Dynamic Pupilometers Using Television Camera System" (incorporated herein by reference). The Stark et al. system employed a television camera system, a digital computer system, an infrared light source, and a visual light stimulator for determining the instantaneous size of a pupil as an eye (or neurologic pupilary control system) of a patient was exposed to various stimuli. Like the early Stark et al. system, conventional pupilometers measure, for example, the diameter of a pupil before and after the pupil is exposed to a light stimulus pulse and also measure the rates at which the pupil may constrict and dilate in response to the initiation and termination of the light stimulus pulse. Pupilometers may comprise hand-held units or, alternatively, may comprise desk or table-mounted, stand-alone units. Pupilometers also generally include some mechanism for ensuring that an imager within the pupilometer is properly positioned in relation to a pupil to be imaged. For example, U.S. Pat. No. 5,646,709 (incorporated herein by reference), issued to Elbert P. Carter, describes an electronic centering system for ensuring that a pupilometer is properly positioned in relation to a pupil to be imaged. Similarly, U.S. Pat. No. 5,187,506 (incorporated herein by reference), issued to Elbert P. Carter, describes an eye orbit housing for ensuring proper positioning between a pupilometer and an eye of a subject prior to the initiation of a pupilary scanning procedure.

Those skilled in the art will appreciate, however, that for a pupilometer to have maximum utility maximum flexibility should be provided for positioning the imager. For example, in the case of a hand-held system few, if any, restrictions should be placed upon the orientation of the imager prior to enabling an imaging function. The reason for this is that medical personnel at, for example, an accident site may have difficulty in positioning an imager in a prescribed position for acquiring pupilary response data. Thus, it is believed that, for hand-held units in particular, a need exists within the pupilometer field for improved data acquisition and processing systems and methods, as such systems and methods may substantially reduce system dependence on imager orientation and may allow pupilometers to become more user friendly.

Similarly, those skilled in the art will appreciate that a need exists for pupilometers that are capable of evaluating more than a mere pupilary response to light stimulus pulses. For example, it is believed that a substantial need exists for a pupilometer that is capable not only of measuring changes in pupilary diameter in response to one or more light stimulus pulses, but also of evaluating pupil shape and/or segmental responses to a visual stimulus. Stated somewhat differently, it is believed that a substantial need exists for a pupilometer having a pupilary shape irregularity or non-uniformity detection capability.

Finally, it is believed that a substantial need exists for pupilometer-based diagnostics systems, as such systems may provide medical practitioners with a cost effective, non-invasive means for gathering and assessing numerous physiologic parameters.

For example, the present invention can be used to screen for Glaucoma, which is the second leading cause of blindness in the world. Visual field perimetry is presently used for diagnosing Glaucoma. In visual field perimetry, a white background and multiple green flicker sources are used. The green sources are randomly turned on for approximately one second durations and the subject patient is asked to press a button if he/she sees a green light. The procedure is repeated until the entire visual field is mapped for each eye. Loss of visual field sensitivity is indicative of Glaucoma.

The current standard of care for Glaucoma detection, however, suffers form inaccuracy and human/patient error. The current standard of care relies on the patient to respond to his or her visual detection of green light by pressing a button. The patient has a limited window of time in which to respond to the green light. Thus, if the patient is not concentrating or responds too quickly or too slowly, the perimetry device will not register the patient's response, and the accuracy of the diagnosis is compromised. Furthermore, current perimetry devices are large machines that are immobile. They are for use in doctors' offices only. Thus, a need exists for improved systems and methods for Glaucoma detection, and the present invention meets these needs and solves the problems associated with standard techniques.

Another area of diagnostic need relates to assessing the level of brain function to diagnose disorders such as autism, age-related disorders, and drug impairment or intoxication. Neurological exams today do not typically include pupilometry beyond the use of a pin-light. Currently, expensive and/or time-consuming tests are required to diagnose impairment of brain function. And, the pin-light test is subjective, non-quantifiable, and inaccurate. The present invention solves these by providing a method and system to closely track the pupil while presenting the eye with a moving visual stimuli to determine the level of coordination. The present invention is capable of quantifying tracking errors, which might occur in the course of a neurological exam, and reduces the subjectivity and increases the repeatability of exams to assess brain function.

Another area of diagnostic need is diagnosis of neurological disease or trauma. Dermatome mapping of patients is commonly done with a pin-prick to determine the level of dorsal root or spinal cord injury. This test, however, is subjective and usually requires cognitive response from a patient. There exists a need for noninvasive diagnosis of neural damage or trauma. The present invention fills that need by providing a means of quantitatively measuring pupilary response to noxious stimulation. Furthermore, this invention is useful in diagnosing dorsal root and spinal cord injuries in unconscious patients with no cognitive response capabilities. It is further useful in diagnosing and monitoring the progression of demyelinating diseases such as multiple sclerosis, which affects conduction velocity through nerve fibers. In addition, testing the level of epidural anesthetic block may be accomplished using pupilometry with this automated stimulus control.

Finally, an area of diagnostic need relates to testing the functional integrity of auditory pathways, i.e., hearing screening. Particularly with infants, hearing has been subjectively screened using stimuli such as in a clap test while observing the startle response. Other tests, such as EEG-type brain stem audible evoked potential (AEP) monitoring systems have been used, but require attachment of electrodes to the scalp and are cumbersome to use. Middle ear tone-feedback monitoring is also used, but is not capable of measuring latency information. The present invention solves these and other problems associated with the prior art by providing hearing screening using objective pupilometer-based testing systems and methods. The pupilometer-based systems are not cumbersome, are easy to use and provide latency information for diagnosing and monitoring the progression of demyelinating diseases.

SUMMARY OF THE INVENTION

In one particularly innovative aspect, the present invention is directed toward a pupilometer having a pupil shape irregularity detection capability. For example, a pupilometer in accordance with the present invention may comprise an imaging sensor for generating signals representative of a pupil of an eye, a data processor coupled to the imaging sensor, and a program executable by the data processor for enabling the data processor to process signals received from the imaging sensor and to thereby identify one or more regions of non-uniformity or irregularity within an image of a perimeter of the imaged pupil.

In one presently preferred embodiment, the one or more regions of pupilary non-uniformity or irregularity are identified by identifying a center point of a pupil and determining a plurality of radii representing distances from the center point to the perimeter of the pupil along a respective plurality of angles in a R,θ coordinate system.

In another innovative aspect, the present invention is directed to a medical diagnostics system incorporating a pupilometer and medical database for correlating actual or derived pupilary image analysis data with stored medical data to formulate medical diagnoses, and to methods of implementing and utilizing such a diagnostics system.

In still other innovative aspects, the present invention is directed to improved thresholding and image data processing algorithms for use within a pupilometer. For example, a pupilometer in accordance with the present invention may utilize a plurality of row and column histogram data sets in an iterative fashion to identify a preferred threshold value for locating the pupil of an eye within an image data frame.

A pupilometer in accordance with the present invention may also process image frame data to determine a shape and/or diameter of the sclera/iris border of an eye and, thereafter, use the determined shape or diameter to evaluate an orientation of the eye of the patient and/or to correlate measured units with defined units of measurement.

When provided with an additional armature supporting, for example, a visible light emitting diode (LED), a pupilometer in accordance with the present invention may be used to measure afferent or consensual pupilary responses to visual stimulus pulses. In such embodiments, a visual stimulus is applied to an eye under examination, and the response of the monitored pupil is recorded and evaluated. Then, as the monitored pupil is allowed to dilate, a stimulus pulse is applied to the other eye of the patient, to see whether or not the monitored pupil again constricts. Following the second stimulus pulse, the monitored pupil is allowed again to dilate, and a final visual stimulus is applied to the eye under examination. During the final stimulus pulse, the constrictive response of the monitored pupil (or lack thereof) is again measured. By measuring the response of the monitored pupil to each stimulus pulse, it is possible to detect retinal impairment in each eye of the patient.

In another innovative aspect, the present invention is directed to a medical diagnostics system incorporating a pupilometer, which can be used to screen for Glaucoma, and for methods of implementing and utilizing such a diagnostics system. This system comprises a pupilometer comprising an imaging sensor for generating signals representative of a pupil of an eye, a data processor, and a program executable by said data processor for enabling said data processor to process signals received from said imaging sensor and to thereby identify the pupil's dynamic response to a light stimulus. The program is further capable of storing the pupil's response data and comparing it to a database of normal measurements to determine if the test responses fall out of range. Alternatively, the program can transmit the data to a microprocessor or peripheral computer, which has stored therein a database of normal measurements, and wherein the microprocessor or peripheral computer is capable of comparing the pupil's response data to the database of normal measurements and providing conclusions as to whether the pupil's response data falls outside of the norm and indicates Glaucoma.

In another innovative aspect, the present invention is directed to a medical diagnostics system incorporating a pupilometer for detecting elevated intracranial pressure, and for methods of implementing and utilizing such a diagnostics system. This system comprises a pupilometer for generating a light source and projecting it to the eye and obtaining data descriptive of one or more pupilary characteristics. The system can further comprise a database for storing data descriptive of one or more pupilary characteristics, and a central processing unit, which may be coupled to the pupilometer, for comparing the data obtained by the pupilometer to the data stored within the database such that the comparison will reveal whether the occulomotor nerve (CNIII) is compromised, thus indicating elevated intracranial pressure.

An exemplary embodiment of the invention is illustrated by a method of detecting elevated intracranial pressure. The method comprises the steps of: providing a pupilometer, wherein the pupilometer comprises a light source that is amplitude modulated; continuously projecting light generated by the light source for a given length of time onto the eye of a patient in a predetermined pattern of amplitude modulation; obtaining, using the pupilometer, a first set of data representative of the pupil's response to the modulated light; storing within a database a second set of data representing pupilary response to light stimulus received in said predetermined pattern of amplitude modulation; and comparing within a data analysis system said first set of data with said second set of data in order to determine whether the occulomoter nerves are compromised, thus indicating intracranial pressure.

In another innovative aspect, the present invention is directed to a medical diagnostics system incorporating a pupilometer for assessing the level of brain function, and for methods of implementing and utilizing such a diagnostics system. This aspect of the invention provides a system comprising a pupilometer for obtaining data descriptive of one or more pupilary characteristics from a subject. The pupilometer may comprise means for providing a visual field to the subject such as a light generated from a visual light source. The system further comprises a database for storing data descriptive of a plurality of pupilary characteristics associated with a set pattern of visual field movement, and a central processing unit coupled to the pupilometer and the database for comparing the data obtained by the pupilometer to the data stored within the database to assess the subject's level of brain function.

In another innovative aspect, the present invention is directed to a medical diagnostics system incorporating a pupilometer for testing the functional integrity of afferent peripheral and cranial pathways as well as testing efferent cranial nerve involvement in patients with afferent pupilary defects, and for methods of implementing and utilizing such a diagnostics system. This system and associated method comprise a pupilometer as previously described, for obtaining data descriptive of a plurality of pupilary characteristics from an eye of a patient. The system further comprises a database for storing data descriptive of a plurality of pupilary characteristics, and a central processing unit coupled to the pupilometer for comparing the data obtained by the pupilometer to the data stored within the database such that neurological disease or trauma may be diagnosed based upon that comparison. The pupilary characteristics being compared may be the amplitude of the pupilary response to a noxious stimulus or the velocity of pupilary response to a noxious stimulus. The method associated with this aspect of the invention comprises the steps of providing a pupilometer, and obtaining, using the pupilometer, pupilary response data from the eye of a patient. The pupilary response data can represent one or more pupilary response characteristics of the eye being tested. The method can further comprise the steps of storing within a database data representative of a plurality of pupilary response characteristics, and comparing with a data analysis system the pupilary response data obtained from the patient with the stored data to determine whether neurological disease or trauma is indicated.

In another innovative aspect, the present invention is directed to a medical diagnostics system incorporating a pupilometer for testing the functional integrity of auditory pathways, and for methods of implementing and utilizing such a system. The system comprises a pupilometer for obtaining data descriptive of one or more pupilary characteristics of an eye of a patient, as described herein. The system further comprises a sound generating transducer in connection with an ear-piece, wherein the transducer is synchronized to the pupilometer such that images of the eye are captured by the pupilometer in sequence with the generation of sound. Thus, hearing can be tested in a quantifiable and objective manner by analyzing pupilary response rather than relying on the patient to consciously respond to the stimulus.

A method for testing the functional integrity of auditory pathways comprises the steps of providing a pupilometer as described herein, providing a sound generating transducer in connection with an ear-piece, and obtaining, using the pupilometer, a first set of data descriptive of one or more pupilary characteristics from an eye of a patient or subject. The method may further comprise the steps of storing within a database a second set of data descriptive of a plurality of one or more pupilary characteristics associated with pupilary response to sound, and comparing within a data analysis system the first and the second sets of data to determine whether the subject's hearing is impaired.

Other objects and features of the present invention will become apparent from consideration of the following description taken in conjunction with the accompanying drawings.

BRIEF DESCRIPTION OF THE DRAWINGS

FIGS. 7A and 7B are illustrations of histogram data sets that may be developed in accordance with a preferred thresholding algorithm utilized by a pupilometer in accordance with the present invention.

Description of Preferred Embodiments

Figure 1:
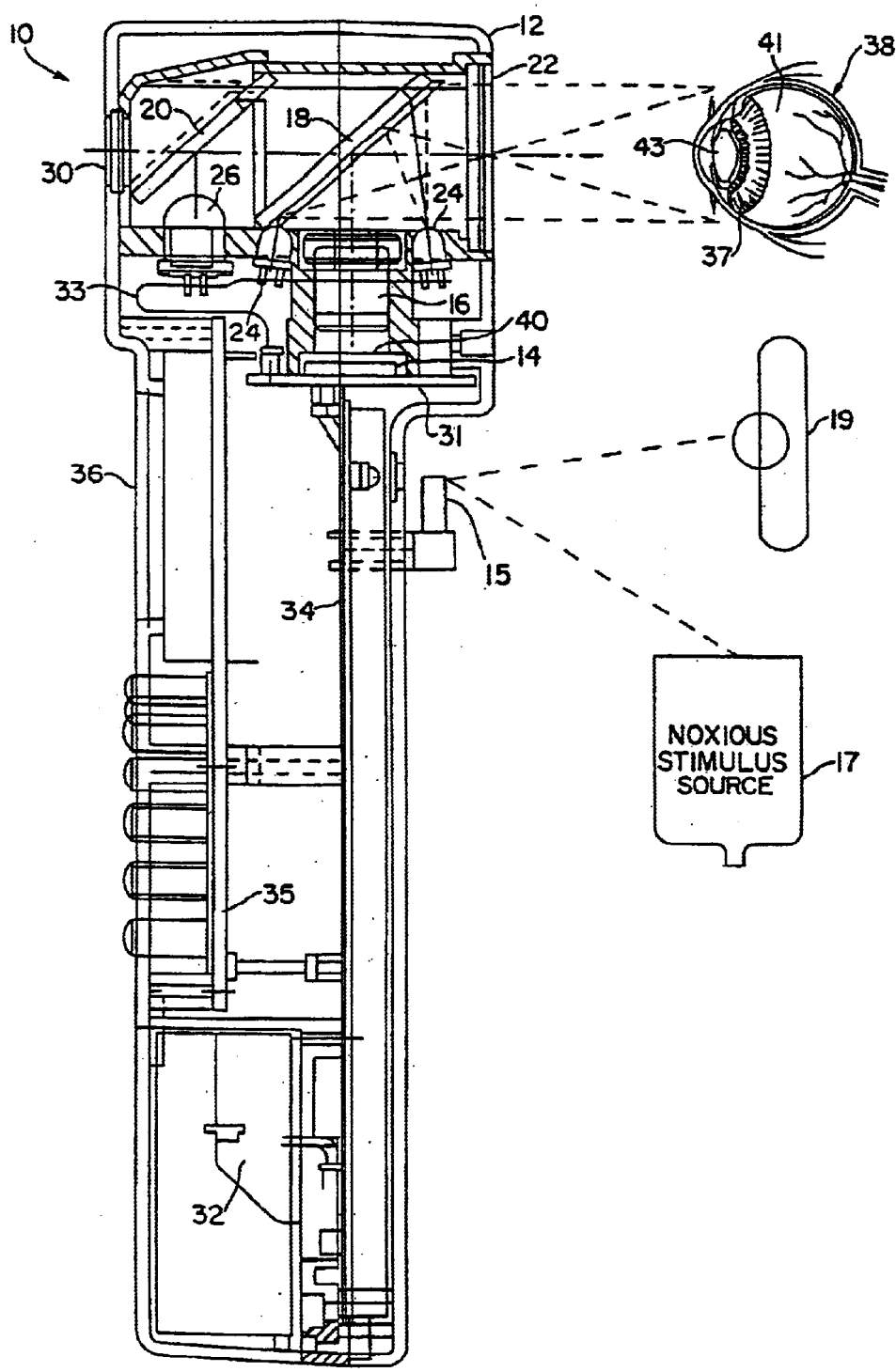
FIG. 1 is a cross-sectional view of a hand-held pupilometer in accordance with a preferred form of the present invention.
Figure 2:
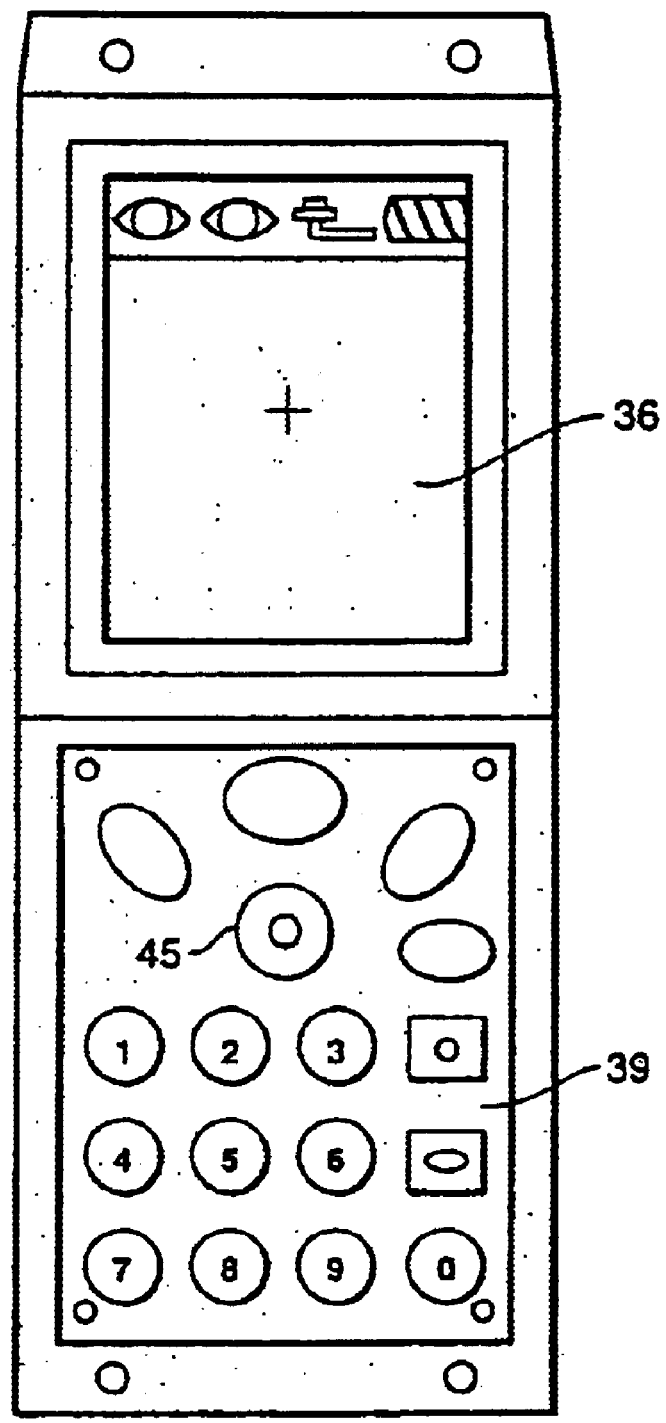
FIG. 2 is an illustration of a liquid crystal display and keypad that may be provided on a hand-held pupilometer in accordance with the present invention.

A. Hardware Components of a Pupilometer in Accordance with the Present Invention Turning now to the drawings, FIG. 1 provides a cross-sectional view of a hand-held pupilometer 10 in accordance with the present invention. FIG. 2 provides an illustration of a liquid crystal display and key pad that may be provided on the hand-held pupilometer 10, and FIG. 3 is an enlarged cross-sectional view of an imaging section of the hand-held pupilometer 10.

Figure 3:
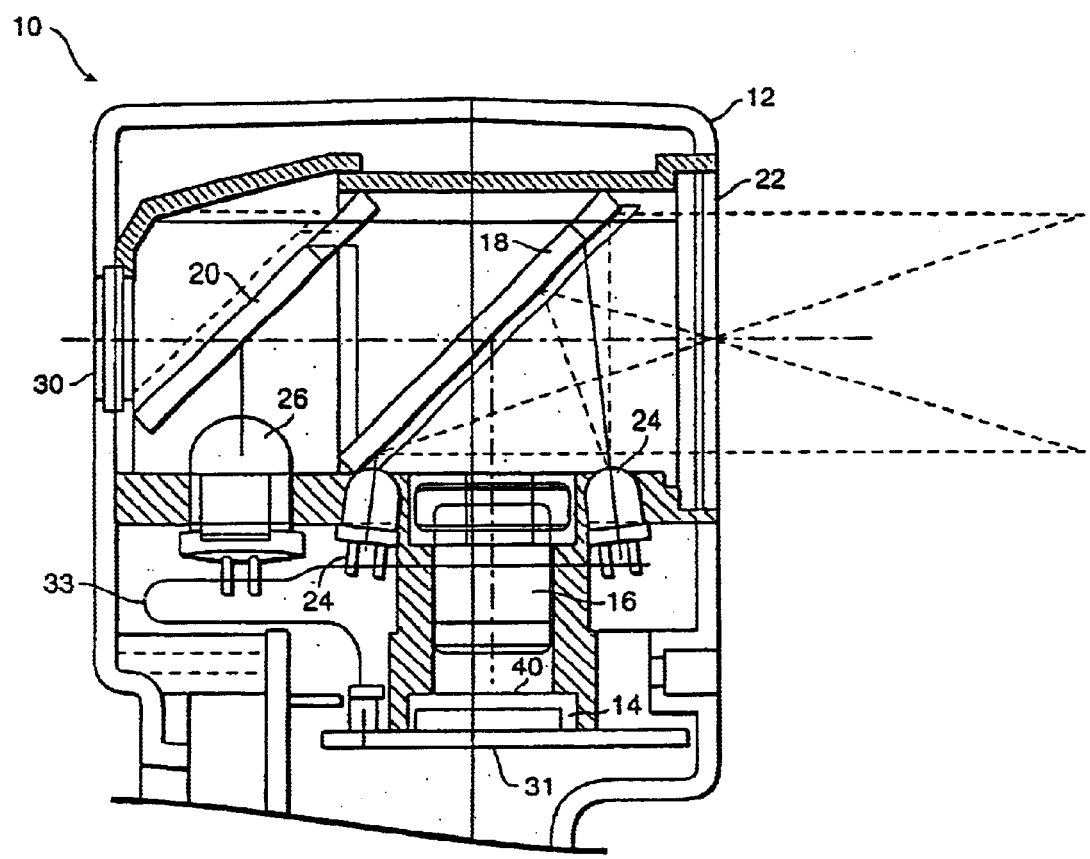
FIG. 3 is an enlarged cross-sectional view of an imaging section of a hand-held pupilometer in accordance with the present invention.

As shown in FIGS. 1–3, the pupilometer 10 preferably includes a housing 12 wherein an imaging sensor 14, an objective lens 16, first and second beam splitters 18 and 20, a shield 22, four infrared (IR) LEDs 24, two yellow LEDs 26, a blue LED 28 (shown in FIG. 4), a reticle 30, a battery 32, an image signal processing board 34 and a liquid crystal display 36 are mounted. Stated somewhat differently, the pupilometer may comprise a viewing port (reticle 30 and shield 22), an imaging system (objective lens 16, imaging sensor 14 and related image processing electronics), an illumination system (IR LEDs 24, blue LED 28 and related control circuitry) and a stimulus system (yellow LEDs 26 and related control circuitry).

Figure 10:
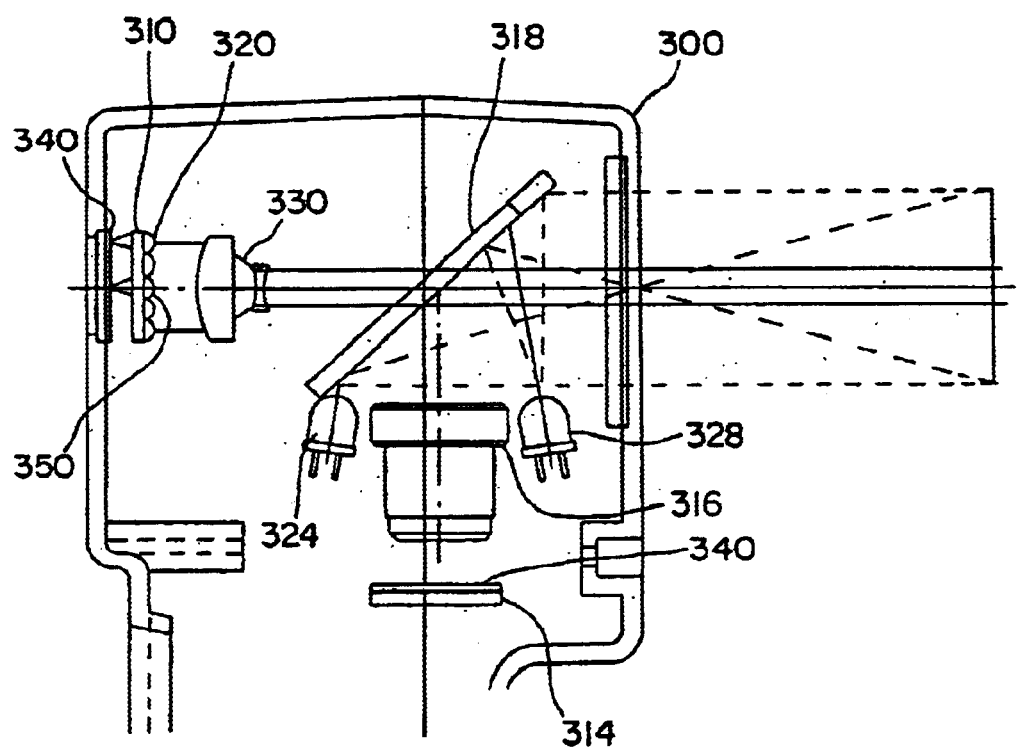
FIG. 10 is a cross-sectional view of a hand-held pupilometer in accordance with yet another embodiment of the present invention.
Figure 13:
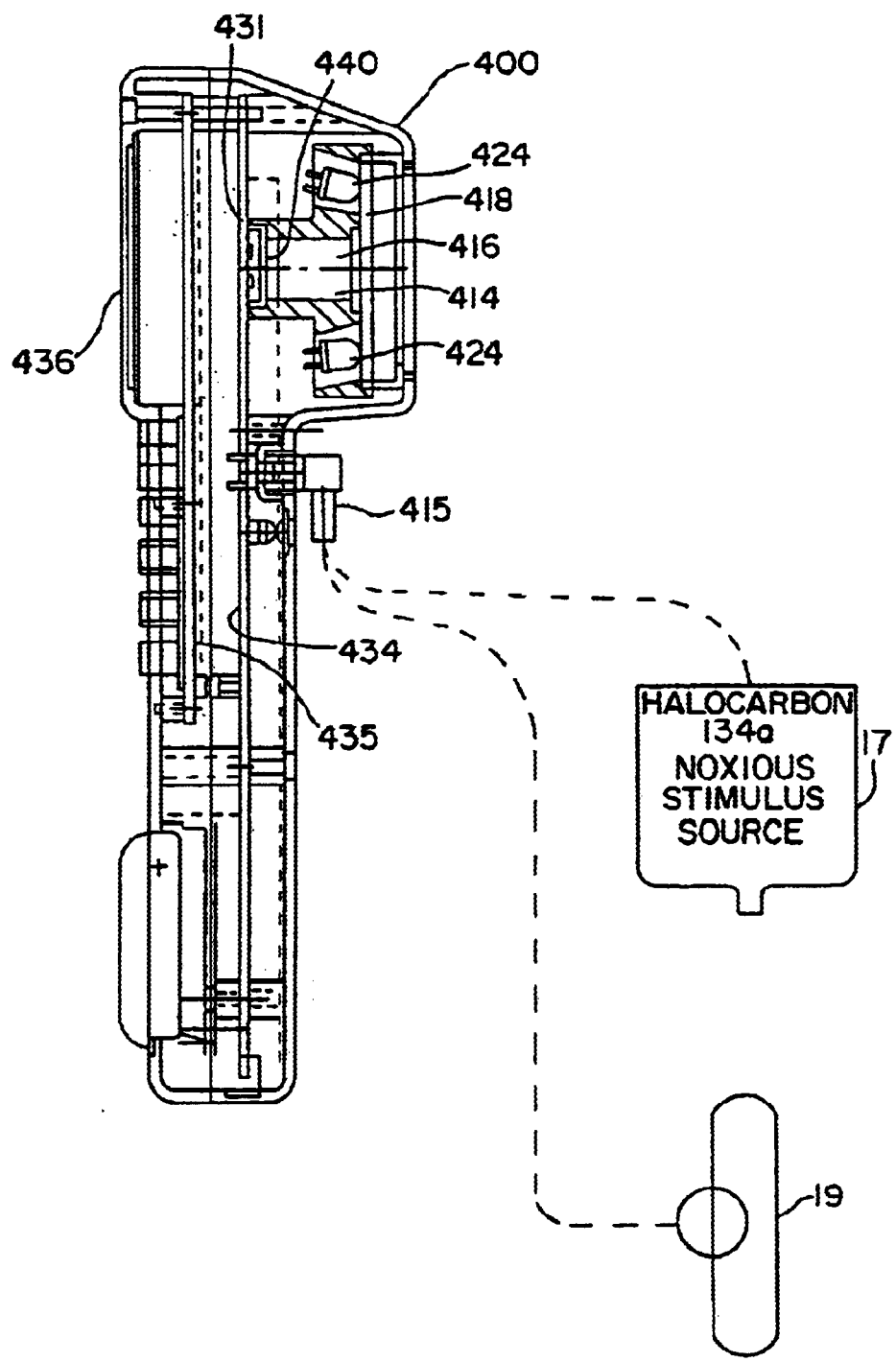
FIG. 13 is a cross-sectional view of a direct-view hand-held pupilometer in accordance with another embodiment of the present invention.

Other embodiments that include some or all of the aforementioned elements are shown in FIGS. 10 and 13. In FIG. 10, the pupilometer 300 further includes a lenslet array 330, and a diode array 340. In FIG. 13, the pupilometer 400 has all of the components of the pupilometer 10, except that it does not have beam splitters, a viewing reticle, blue LEDS, or yellow LEDS. It does, however, contain white LEDS, now shown, a filter glass 418, and an auxiliary connecter 415.

1. The Viewing Port

The viewing port (reticle 30 and shield 22) is provided to aid a user in properly positioning the pupilometer 10 for initial data acquisition. By looking through the reticle 30 and shield 22, the user of the pupilometer 10 is able to properly position the pupilometer 10 in front of an eye 38 of a patient, such that an image of the pupil of the patient's eye may be projected onto the imaging sensor 14. The reticle 30 preferably has circular targets (not shown) silk screened or etched on one surface. The targets are positioned along the user's line of sight so as to appear concentric with the iris and pupil of an eye 38 under observation.

Those skilled in the art will appreciate that the reticle 30 and shield 22 also serve as environmental barriers and function to minimize exposure of the imaging system to caustic cleaning agents, biological material and airborne dust, all of which can have a negative impact upon the performance of the imaging system.

Pupilometers 300 and 400, as shown in FIGS. 10 and 13 respectively, do not contain a viewing port as described in connection with pupilometer 10. In pupilometers 300 and 400, the reticle and viewing port have been replaced by functions of the LCD. For example, in FIG. 13, the LCD 436 provides a low frame rate image of the eye during the targeting procedure with graphical indications that the software has detected the iris and pupil. The frame rate can be 6 frames per second, more preferably 10 frames per second, more preferably 25 frames per second, more preferably 50 frames per second, more preferably 100 frames per second, more preferably 200 frames per second, and most preferably 500 frames per second.

An electronic window, which helps the user center the subject's eye, is also provided during the targeting phase. In the process of targeting, an image of the eye is displayed on the LCD 436. Graphical aids, such as black lines or boxes are displayed to help position the device over the eye. The image on the LCD is updated at a rate of about 6 frames per second, more preferably 10 frames per second, more preferably 25 frames per second, more preferably 50 frames per second, more preferably 100 frames per second, more preferably 200 frames per second, and most preferably 500 frames per second.

The LCD 436 can be monochromatic or color. A color LCD 436 can improve the targeting process by providing graphical feedback about the quality of the tracking/imaging in a different color than that represented by the eye.

2. The Imaging System

The imaging sensor 14 preferably comprises a N×M bit CMOS imaging sensor of a type that is commercially available. One such imaging sensor is the 384×288 bit, Model OV5017, CMOS imaging sensor manufactured and distributed by Omnivision Technologies, Inc. of Sunnyvale, Calif. The imaging sensor 14 is mounted to an imager board 31 of the pupilometer 10 and is coupled to a microprocessor (not shown) provided on a main processing or mother board 34 of the pupilometer 10. This allows for direct capture of digital images. Images in the form of 8 bit (or greater) gray scale bit maps are stored in system memory for image analysis and display on the liquid crystal display 36 (shown in FIG. 2). The microprocessor (not shown) preferably comprises an Elan SC 400 manufactured and distributed by Advanced Micro Devices, Inc., of Austin, Tex.

The imaging system of the present invention is designed such that, when the hand-held pupilometer 10 is positioned in front of the eye 38 of a subject, a properly illuminated and in-focus image of the pupil 43 of the subject's eye 38 is obtained at the sensor plane 40 of the pupilometer 10. The objective lens 16 and a first beam splitter (i.e., wavelength selective filter) 18 preferably are used to focus an image of the pupil 43 of the subject's eye 38 on the sensor plane 40. In a preferred form, the objective lens 16 comprises a five element lens having a focal length of 7.0 mm. The first beam splitter 18 preferably comprises a glass substrate having a thickness of 1.6 mm that is coated with a multi-layer dielectric coating (not shown) to form a wavelength selective filter. The subject side 42 of the beam splitter 18 is coated to enhance reflection at the blue and infrared (IR) wavelength bands with a 45° angle of incidence. The user side 44 of the beam splitter 18 is AR coated to minimize effects resulting from multiple reflections in the image path.

Thus, as shown in FIGS. 1 and 3, the beam splitter 18 functions to direct blue and/or IR light generated by the blue and IR LEDs 28 and 24, respectively, toward the eye 38 of a patient and to provide a return path to the imaging sensor 14 for blue and/or IR light that is reflected from the eye 38 of the patient.

The microprocessor (not shown) provided on the main signal processing board 34 controls the operation and function of the various components comprising the imaging system as described more fully below.

The imaging system of the pupilometer 300 shown in FIG. 10 is similar to that described with respect to pupilometer 10. The beam splitter 318, imaging sensor 314 including imaging plane 340, and objective lens 316, each can be of the same type as beam splitter 18, imaging sensor 40 including imaging plane 14, and objective lens 16 respectively. The objective lens 316 and beam splitter 318 are used to focus an image of the pupil of the subject's eye on the sensor plane 340.

Pupilometer 400, as shown in FIG. 13, functions in the same manner except that a beam splitter is not needed to direct an image of the pupil of the subject's eye on the sensor plane 440. Light passes through filter glass 418 and objective lens 416, which together focus an image of the pupil on sensor plane 440. The sensor plane 440 is part of the imaging sensor 414. Furthermore, the filter glass 418 is in direct contact with and mounted on the objective lens 416. The filter glass 418 can remove all spectral components except for IR light. It can also improve the image contrast at the sensor and reduce variation in ambient light conditions, which can also affect performance.

Thus, as shown in FIG. 10, the beam splitter 318 functions to direct blue and/or IR light generated by the blue and IR LEDS, 328 and 324 respectively, toward the eye of a patient, and to provide a return path to the imaging sensor 314 for blue and/or IR light that is reflected from the eye of the patient.

The Illumination System

With respect to pupilometers 10, 300, and 400, the illumination system preferably comprises a blue light emitting diode (LED) 28 and 328 respectively (not shown with pupilometer 400 in FIG. 13), and four infrared (IR) LEDs 24, 324, and 424 respectively. Although not shown in pupilometer 400, it too can include a blue LED mounted in the same manner as in pupilometers 10 and 300. The IR LEDs 24, 324, and 424 preferably are arranged symmetrically about the objective lens 16, 316, and 416 respectively. The IR LEDs 24 and blue LED 28 are coupled to a flex circuit 33 that is coupled to the main signal processing board 34 of pupilometer 10. Although not shown in FIGS. 10 and 13, the same is true for pupilometers 300 and 400. When activated by the microprocessor (not shown), the IR LED's 24 emit IR light preferably having a wavelength of substantially 850 nm. Again, this is also true with respect to the IR LEDS in pupilometers 300 and 400. Thus, those skilled in the art will appreciate that the emission bandwidth of the IR LEDs lies beyond the physiological response of the human eye but within the photoelectric response of the imaging sensors 14, 314, and 414. Stated somewhat differently, while the human eye is unable to detect the IR light emitted by the IR LEDs, IR light generated by the IR LEDs and reflected by the eye 38 of a subject may be detected by the imaging sensors.

Figure 4:
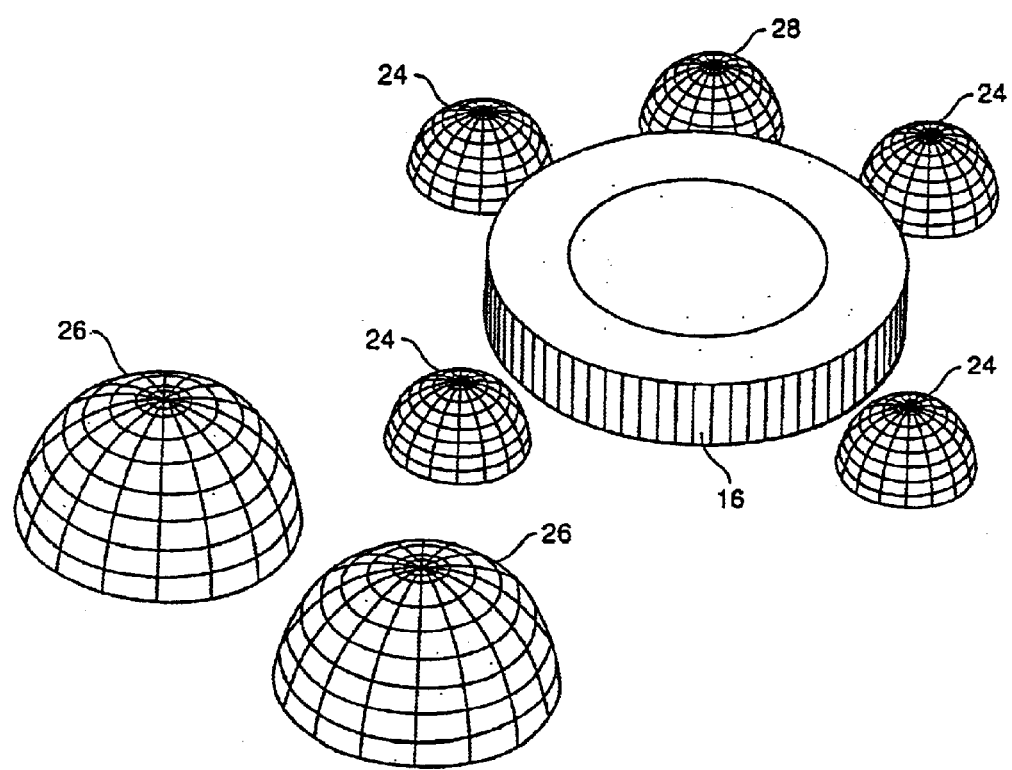
FIG. 4 is a three-dimensional plan view showing a preferred arrangement of a plurality of IR, blue and yellow LEDs that may be used for ocular illumination and stimulation within a pupilometer in accordance with the present invention.

The four IR LEDs 24, 324, and 424 in each of pupilometers 10, 300, and 400 respectively, preferably are arranged in diametrically opposed groups of two, as shown in FIG. 4. By arranging the IR LEDs in the manner shown in FIG. 4, it is possible to more precisely control the IR illumination of a patient's eye 38 and, moreover, to achieve levels of 0, 50 and 100% illumination, if desired. Again, this desired arrangement applies equally to pupilometers 300 and 400. The only difference with pupilometers 300 and 400 is that they do not have yellow LEDS 26, but instead have white LEDS, which are not shown in FIGS. 10 and 13, but which are disposed around objective lenses 316 and 416 in the same manner as yellow LEDS 26 are disposed around objective lens 16.

The blue LEDs are used for ocular illumination in situations where the sciera/iris border of a patient's eye 38 may be difficult to detect with IR illumination alone. As shown in FIG. 4, the blue LED 28 preferably is placed on the same radial arc that is defined by the IR LEDs 24, which surround the objective lens 16. The blue LED 28, when activated by the microprocessor (not shown), preferably emits light having a wavelength of substantially 470 nm. The same is true for the blue LEDS associated with pupilometers 300 and 400. Thus, blue LEDS 328 are preferably placed on the same radial arc that is defined by the IR LEDS 324, which surround the objective lens 316. Blue LEDS 328 also emit light having a wavelength of substantially 470 nm. And the blue LEDS associated with pupilometer 400 (not shown) also emit a light having a wavelength of substantially 470 nm, and are also preferably placed in an arc that is defined by the IR LEDS 424, which surround objective lens 416.

It has been discovered by the inventors hereof that light in the blue color band may be used to substantially improve sclera/iris border image contrast because the iris 37 and sclera 41 of a subject's eye 38 generally have substantially different light absorption and reflection characteristics in the blue color band. Thus, the use of a blue LED for sclera/iris border imaging is believed to be a particularly innovative aspect of the present invention.

Because the human eye is responsive to blue radiation, the blue LEDs preferably are only activated for brief periods of time in relation to the temporal response of a subject's eye 38 or, alternatively, is used in conjunction with the stimulus LEDs 26 (not shown with pupilometers 300 and 400) described below. Moreover, in a preferred form, IR and blue light illumination of the eye 38 of a subject may be performed in a multiplexed fashion, such that the eye of the subject is illuminated with IR light for a first period of time and, thereafter, illuminated with blue light for a second period of time. This is discussed more fully below with reference to FIG. 6.

The microprocessor (not shown) provided on the main signal processing board 34 controls the operation and function of the various components comprising the illumination system as described more fully below.

4. The Stimulus System

The stimulus system of the pupilometer 10 comprises two yellow LEDs 26 and a second beam splitter 20. The yellow LEDs 26 preferably are coupled to the flex circuit 33 and, when activated by the microprocessor (not shown), emit light having a wavelength of substantially 570 nm. Like the first beam splitter 18, the second beam splitter 20 preferably comprises a glass substrate having a thickness of 1.6 mm and is coated with a multi-layer dielectric coating (not shown) to form a wavelength selective filter. The subject side 50 of the beam splitter 20 is coated to enhance reflection at the yellow wavelength band with a 45° angle of incidence, and the user side 52 of the beam splitter 20 is AR coated to minimize effects resulting from multiple reflections in the user's observation path. The stimulus system of the pupilometer 10 preferably provides on-axis illumination of the pupil 43 of the eye 38 of a patient, as shown in FIG. 1.

The stimulus system of pupilometer 300 can comprise yellow LEDS as in pupilometer 10, or white LEDS (not shown). These yellow or white LEDS operate in the same manner as those in pupilometer 10. Additionally, however, pupilometer 300 includes a lenslet array 330, and a diode array 340, which add an additional stimulus function. The diode array 340 functions in the detection of glaucoma by providing blue light from series N concentrated (optically) blue LEDS 320, which can be imaged onto the retina in such a way as to stimulate N specific regions of the retina. The lenslet array 330 focuses the light through the beam splitter 318 appropriately so that the blue light that is emitted reaches a known area of the retina. Furthermore, the diode array 340 has a diffuse yellow light emitting surface 310 to bias the background as yellow against the blue flicker sources 320.

The stimulus system of pupilometer 400 can also comprise yellow LEDS as in pupilometer 10, but more preferably comprises white LEDS (not shown). In pupilometer 400, there are four white LEDS that are placed symmetrically among the IR LEDS 424. Thus, a total of eight LEDS are placed around the objective lens 416 on a common radial displacement from the optical axis of the objective lens 416.

B. Software Components of a Pupilometer in Accordance with the Present Invention The following description of the software applies to pupilometers 10, 300, and 400, but will only be described in connection with pupilometer 10 for convenience and brevity. It should be understood, however, that the software and microprocessor components described herein are designed for use with each of the pupilometers disclosed herein.

Figure 5:
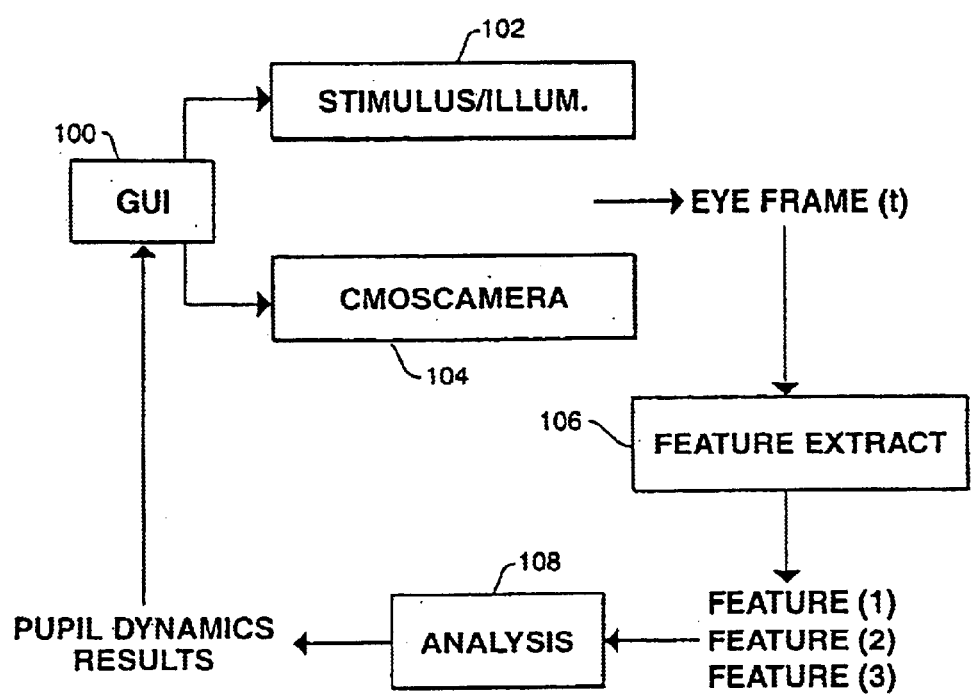
FIG. 5 is a block diagram illustrating a group of programming objects that preferably comprise an operating program of a pupilometer in accordance with the present invention.
Figure 6:
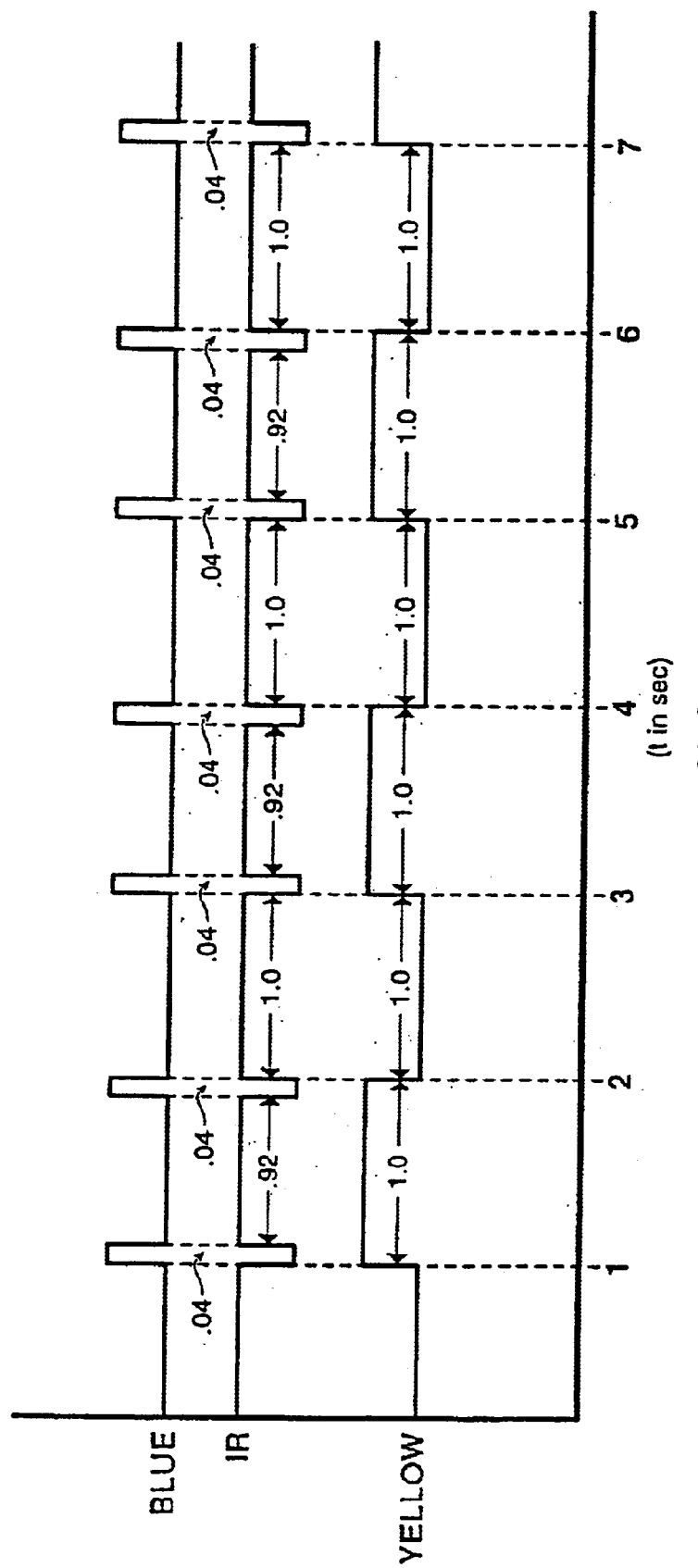
FIG. 6 is a timing diagram illustrating a typical stimulus/illumination sequence for the IR, blue and yellow LEDs that may be used within a pupilometer in accordance with the present invention.

Turning now to FIGS. 5–7, a pupilometer 10 in accordance with the present invention is a microprocessor based system and, therefore, preferably includes several software components or modules for controlling its operation. As is well known in the art, an operating system provides fundamental machine level interfaces between the hardware elements comprising the pupilometer 10. More specifically, various device drivers are used to provide an interface between the microprocessor (not shown) and the imaging sensor 14, IR =LEDs 24, yellow LEDs 26, blue LED 28, keypad 39 and liquid crystal display 36.

The highest level of programming or code used within the pupilometer 10 is referred to herein as the P-Program, and the P-Program preferably is divided into five principal objects corresponding to different hardware and mathematical components. The five principal objects are illustrated in block diagram form in FIG. 5 and preferably include a graphic user interface (GUI) object 100, a stimulus/illumination object 102, a CMOS camera object 104, a feature extraction object 106 and an analysis object 108. All of the above-listed objects preferably are developed in Microsoft Visual C++ and Windows CE, and the graphic user interface (GUI) object 100 preferably is based on Win32 Api functions that are available in Windows CE. Visual C++ and Windows CE are software products distributed by Microsoft Corp. of Redmond, Washington.

1. Graphic User Interface (GUI) Object

The graphic user interface object 100 allows for data/information exchange between a user and the pupilometer 10. Information relating to the current status of the pupilometer 10 including mode of operation (i.e., direct or consensual response, left or right eye measurement etc.) and the battery level is displayed via the graphic user interface object 100. All inputs and outputs of the pupilometer 10 preferably are coordinated via the graphic user interface object 100. Verification of subject ID numbers and/or patient identification data may be accomplished under control of the graphic user interface object 100. Measurement parameters are determined and set with the assistance of the graphic user interface object 100. Instructions during measurement sequences and images of the iris 37 of the eye 38 of a subject are provided on the liquid crystal display 36 under control of the graphic user interface object 100. Similarly, results of measurement sequences are displayed on the liquid crystal display 36 under control of the graphic user interface object 100, and the option to transfer measurement results to a printer or network computer (not shown) is available through the graphic user interface object 100.

2. Stimulus/Illumination Object

The stimulus/illumination object 102 defines and controls the function of the yellow LEDs 26, IR LEDs 24 and blue LED 28 and, therefore, controls the stimulation and illumination of the eye 38 of a subject. The stimulus/illumination object 102 defines the various light profiles (i.e., yellow, IR and blue) as a function of time and controls activation of the yellow, IR and blue LEDs 26, 24 and 28, accordingly. In a typical stimulus/illumination sequence, the LEDs 26, 24 and 28 preferably are activated in the manner described below. However, those skilled in the art will appreciate that the stimulus/illumination sequence may be varied depending upon the circumstances of any given situation, and that variations in the stimulus/illumination sequence may be effected through the user interface object 100.

During a typical stimulus/illumination sequence, the LEDs 24, 26 and 28 may be operated as shown in FIG. 6. For example, during a typical measurement sequence, the yellow LEDs 26 may be activated and deactivated for successive I second intervals (i.e., "on" for 1 second and "off" for 1 second) for a period of 10 seconds total. Simultaneously, the IR LEDs 24 may be activated for all periods when the yellow LEDs 26 are "off," and may be deactivated, activated and deactivated (i.e., turned "off,""on" and "off") for respective 0.04, 0.92 and 0.04 second intervals, while the yellow LEDs 26 are turned "on." Similarly, the blue LED 28 may be activated, deactivated and activated for respective 0.04, 0.92 and 0.04 second intervals, while the yellow LEDs 26 are turned "on," and may be deactivated during all periods when the yellow LEDs are turned "off." This allows for the operation of the IR LEDs 24 and blue LED 28 to be multiplexed. In such an embodiment, the image frame transfer rate preferably would be set, for example, to 50 frames per second.

3. The CMOS Camera Object

The CMOS camera object 104 controls the transfer of image data frames between the CMOS imaging sensor 14 and memory associated with the microprocessor (not shown) provided on the main signal processing board 34 (i.e., between the imaging sensor 14 and the P-Program). Preferably, the rate of image frame transfer between the imaging sensor 14 and the memory associated with the microprocessor (not shown) may be programmably set within a range from 1 frame per second to 50 frames per second, depending upon the needs and/or desires of the user.

However, those skilled in the art will appreciate that in some instances it may be desirable to provide for faster frame transfer rates, and that such rates might be as high or higher than 100 frames per second. The image frame acquisition or transfer rate is defined by the user under control of the graphic user interface object 100.

4. The Feature Extraction Object

The feature extraction object 106 defines several image processing procedures that are used to isolate a pupil within an image and to extract several pupil features such as size, shape and position from each pupil image data frame. All processing procedures defined by the feature extraction object preferably are performed on each image data frame, with the exception of the automatic thresholding procedure described below. The automatic thresholding procedure is applied during an initial calibration phase and, therefore, does not need to be applied to each image data frame. Rather, the results of the automatic thresholding procedure are used during feature extraction processing for each image data frame. The results of the automatic thresholding procedure also may be used to set and/or adjust image exposure gain settings within the system.

The feature extraction object 106 employs a flying spot processing algorithm to identify the center of the pupil, a fitted circumference and/or radius of the pupil and, preferably, 48 radii representing the distance between the center and perimeter of the pupil at 48 separate angles in an R,θ coordinate system, where θ defines an angular orientation about the center of the pupil, and R represents the radius of the pupil at that orientation. The fitted radius of the pupil is determined by selecting a circumference that best fits a contour of the pupil and by solving the equation 2π r to obtain the radius value (r).

Those skilled in the art will appreciate that, by defining and evaluating 48 distinct radii about the center of the pupil, it is possible in accordance with the present invention to detect one or more non-uniformities or irregularities that may exist around the perimeter of the pupil. It also is possible to characterize the shape of the pupil as circular, elliptical etc. based upon the determined radii. It also is possible to evaluate selected sections of a pupil perimeter to determine whether or not those sections exhibit normal contour characteristics and/or normal responses to visual stimulus. It is believed that these capabilities represent significant improvements over conventional pupilometry systems, as these features allow not only for the performance of conventional pupil aperture and response evaluations, but also for the performance of pupil shape and sectional contour evaluations. Thus, where a particular affliction may produce a defined irregularity in pupil shape or defined sectional response to visual stimulus, the affliction may be identified through the use of a pupilometer in accordance with the present invention.

The inputs to, and outputs obtained from, the flying spot algorithm may be defined as follows:

Input Parameters:
Frame=eye image frame generated by the CMOS imaging sensor 14
Threshold=gray level threshold value; any pixel having a gray scale value greater than the threshold value is considered to be part of the pupil.

Output Parameters:
Output=fitted radius and center of pupil, 48 radii.

It is assumed herein that within the gray scale used by the pupilometer 10 the color black will be associated with a high gray scale value, such as 255, and the color white will be associated with a low gray scale value, such as 0. However, those skilled in the art will appreciate that the relative maximum and minimum values could be reversed.

It is believed that the use of flying spot algorithms are well known in the art and, therefore, that the flying spot algorithm need not be described in detail herein. Nonetheless, the basic flying spot procedure may be described as follows. The flying spot procedure starts with a large circumference centered on the image of an eye and iteratively reduces the size of the circumference. In reducing the size of the circumference and adjusting the center location of the circumference, for each iteration the following momentums will be computed:

$$\mu x = 1/N * \sum_{x,y} \text{gray\_level\_sign}(x, y)(x - x0)$$

$$\mu y = 1/N * \sum_{x,y} \text{gray\_level\_sign}(x, y)(y - y0)$$

$$\mu r = 1/N \sum_{x,y} \text{gray\_level\_sign}(x, y)$$

where N represents the number of pixels having coordinates x,y in the circumference contour; gray_level_sign(x,y) is +1, if the gray level value of the pixel (x,y) is greater than the threshold value; gray_level_sign (x,y) is −1, if the gray level value of the pixel (x,y) is less than the threshold value; and x0,y0 are the center coordinates of the circumference.

The x and y coordinates of the circumference center and the radius are updated as follows:
x0=x0+μx*Gain_x
y0=y0+μy*Gain_y
radius=radius +μr*Gain_r.

As indicated above, the updating procedure is applied iteratively, each time calculating the momentum and then changing the center and radius of the flying spot, such that the circumference finally converges to a circumference that best fits the contour of the pupil.

Once the fitted radius and center of the pupil are determined, 48 radii representing the distance between the center and perimeter of the pupil at 48 separate angles in an R,θ coordinate system preferably are determined, where θ defines an angular orientation about the center of a pupil, and R represents the radius of the pupil at that orientation. By evaluating the 48 determined radii, it is possible to characterize the overall shape of the pupil and to determine whether or not any sectional non-uniformities or irregularities are present about the perimeter of the pupil. Such processing may be performed either by the feature extraction object 106 or the analysis object 108.

Another principal function performed by the feature extraction object is thresholding. The thresholding function automatically identifies a gray level value that separates the pupil from the background in an image data frame. Moreover, when an appropriate threshold value is determined, all pixels having a gray level value greater than the threshold value are considered to comprise part of the image of the pupil, and all pixels having a gray level value less than the threshold are considered to correspond to background.

Preferably, the defined threshold value represents the average of a maximum hypothetical threshold value and a minimum hypothetical threshold value. The maximum and minimum hypothetical threshold values are derived through respective histogram analysis routines. Moreover, as shown in FIGS. 7(*a*) and 7(*b*), for each hypothetical threshold value two histograms are evaluated, one for the rows of pixels within an image frame, and one for the columns of pixels within the image frame. The histogram value for a given row or column is determined by counting the pixel locations in that row or column that have a gray level value that exceeds the hypothetical threshold level. Thus, the number of values within a histogram preferably corresponds to the number of rows or columns in the image data frame, and each value represents the number of pixels in the specific row or column that have a gray level exceeding the hypothetical threshold value.

Turning now in particular to FIGS. 7(a) and 7(b) the hypothetical maximum and hypothetical minimum threshold values are determined by iteratively altering a hypothetical threshold value until a prescribed histogram profile is achieved. An acceptable profile is illustrated in FIG. 7(a) and is one in which a null-high-null pattern is achieved for both a row histogram (y Hist) and column histogram (x Hist). More specifically, an acceptable profile preferably comprises a single "high" bordered by a pair of "nulls." Unacceptable profiles are illustrated, for example, in FIG. 7(b).

The hypothetical maximum threshold value is determined by selecting an absolute maximum value and iteratively decreasing that value and deriving corresponding histogram data sets until acceptable row and column histogram profiles are achieved. Similarly, the hypothetical minimum threshold value is determined by selecting an absolute minimum value and iteratively increasing that value and deriving corresponding histogram data sets until acceptable row and column histogram profiles are achieved. Once the hypothetical maximum and minimum threshold values are determined, those values are averaged to determine the defined threshold value that will be used by the feature extraction object 106. Those skilled in the art will appreciate that the defined threshold value may correspond to the maximum hypothetical threshold value, the minimum hypothetical threshold value, or any value that is between those values. Thus, in alternative embodiments, the defined threshold value could be determined, for example, based on a weighted average of the maximum and minimum hypothetical threshold values. In such an embodiment, the defined threshold value may comprise a value corresponding to the sum of the minimum hypothetical threshold value and $2/3$ of the difference between the maximum and minimum hypothetical threshold values.

5. The Analysis Object

The analysis object 108 analyzes the configuration characteristics of a pupil as a function of time. Preferably, the analysis object 108 receives, as inputs, from the feature extraction object 106 a plurality of data sets for each captured image data frame. The data sets preferably include the time of image capture in msec, x and y coordinates of the pupil center, radius of the flying spot circumference, 48 radii representing the distance between the center and border of the pupil for 48 selected angles within an R,θ coordinate system, and an applied stimulus record for the relevant entry. Upon receiving the input data sets, the analysis object 108 preferably derives at least the following information from the data sets: minimum pupil aperture, maximum pupil aperture, difference between maximum and minimum pupil apertures, latency of pupil response to yellow light stimulus, pupil constriction velocity, first and second pupil dilation velocities and, if desired, pupil irregularity magnitude and location information. Where pupil irregularities are detected, the location of the irregularity preferably is identified by its θ coordinate. However, graphical indications also may be provided on the display 36 of the pupilometer 10.

Further, in alternative embodiments, the analysis object 108 may include programming for effecting a multi-varied analysis wherein a plurality of selected variables including, for example, latency indicia, constriction velocity indicia, first and second dilation velocity indicia, segmental static and/or dynamic analysis indicia, constriction/dilation velocity ratio indicia, and maximum and minimum diameter indicia are evaluated for one or both eyes of a patient to arrive at one or more scalar values that are indicative of an overall physiologic or pathologic condition of the patient or, alternatively, to arrive at one or more scalar values that are indicative of an overall opto-neurologic condition of the patient.

With regard to the information derived by the analysis object 108, the maximum pupil aperture, minimum pupil aperture and difference determinations require the identification of the maximum pupil aperture and minimum pupil aperture within a set of image data frames and, thereafter, computation of the difference between those values. The latency determination provides an indication in milliseconds of the time that it takes for a pupil to begin to respond to a visible (i.e., yellow) light stimulus pulse. Further, those skilled in the art will appreciate that, when a pupil is exposed to a visual light stimulus pulse, the pupil generally will, after some latency period, constrict and, once the stimulus is discontinued, dilate and return to its original size and configuration. Thus, the analysis object 108 evaluates the response of a pupil to a visual stimulus to determine a pupil constriction velocity and evaluates the response of the pupil to termination of the stimulus to determine first and second dilation velocities. First and second dilation velocities are evaluated because a pupil generally will dilate quickly for a first period of time and, thereafter, will dilate more slowly until its original size and configuration are achieved. Finally, as explained above, an analysis object 108 in accordance with the present invention also preferably identifies any irregularities in the shape of the pupil. Such irregularities may be either static or dynamic in nature. For example, a static irregularity may take the form of an irregular pupil shape in ambient light, whereas a dynamic irregularity may take the form of increased latency for a particular section of the pupil during a response to a the initiation or termination of a visual stimulus. With regard to static irregularities, such irregularities may be identified by identifying the angular orientations of radii that do not fall within prescribed limits, differ from other calculated radii by a predetermined deviation or differ from the fitted radius by a predetermined amount, deviation or percentage.

Finally, an analysis object 108 in accordance with the present invention preferably includes programming for identifying statistical anomalies within derived results. This allows an analysis object 108 in accordance with the present invention to discard either actual pupilary response data sets (i.e., fitted radius, center and radii calculations) or derived data sets (i.e., max aperture, min aperture, latency, constriction rate or dilation rates) when a selected value differs from other values by a statistically significant degree. When such anomalies are identified, the relevant data sets are not included in averaging functions, and where many anomalies are identified, an imaging sequence will be invalidated and must be repeated.

C. Operation of a Pupilometer in Accordance with the Present Invention

The following description of the operation of a pupilometer of the present invention applies to each of pupilometers 10, 300, and 400, but will only be described in connection with pupilometer 10 for convenience and brevity. It should be understood, however, that the software and microprocessor components of each of pupilometers 10, 300, and 400 can be the same, and therefore, the operation of each of these pupilometers can be the same.

Figures 8, 8A:
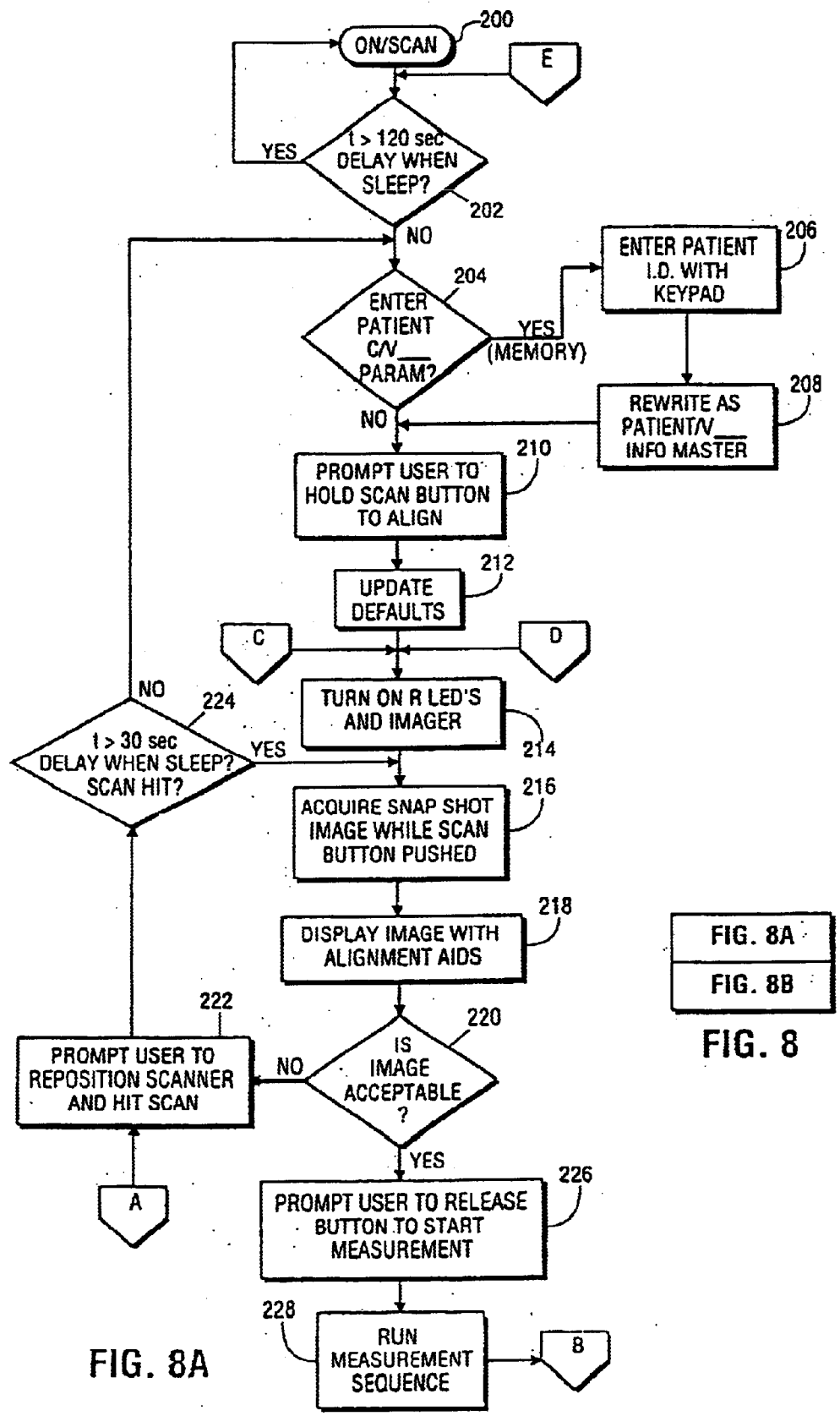
FIGS. 8A and 8B comprise two portions of a flow chart illustrating a basic operating protocol for a pupilometer in accordance with the present invention. The icons labeled "A" through "E" in each of the FIGS. 8A and 8B represent points of continuity between the two portions of the flow chart.
Figure 8B:
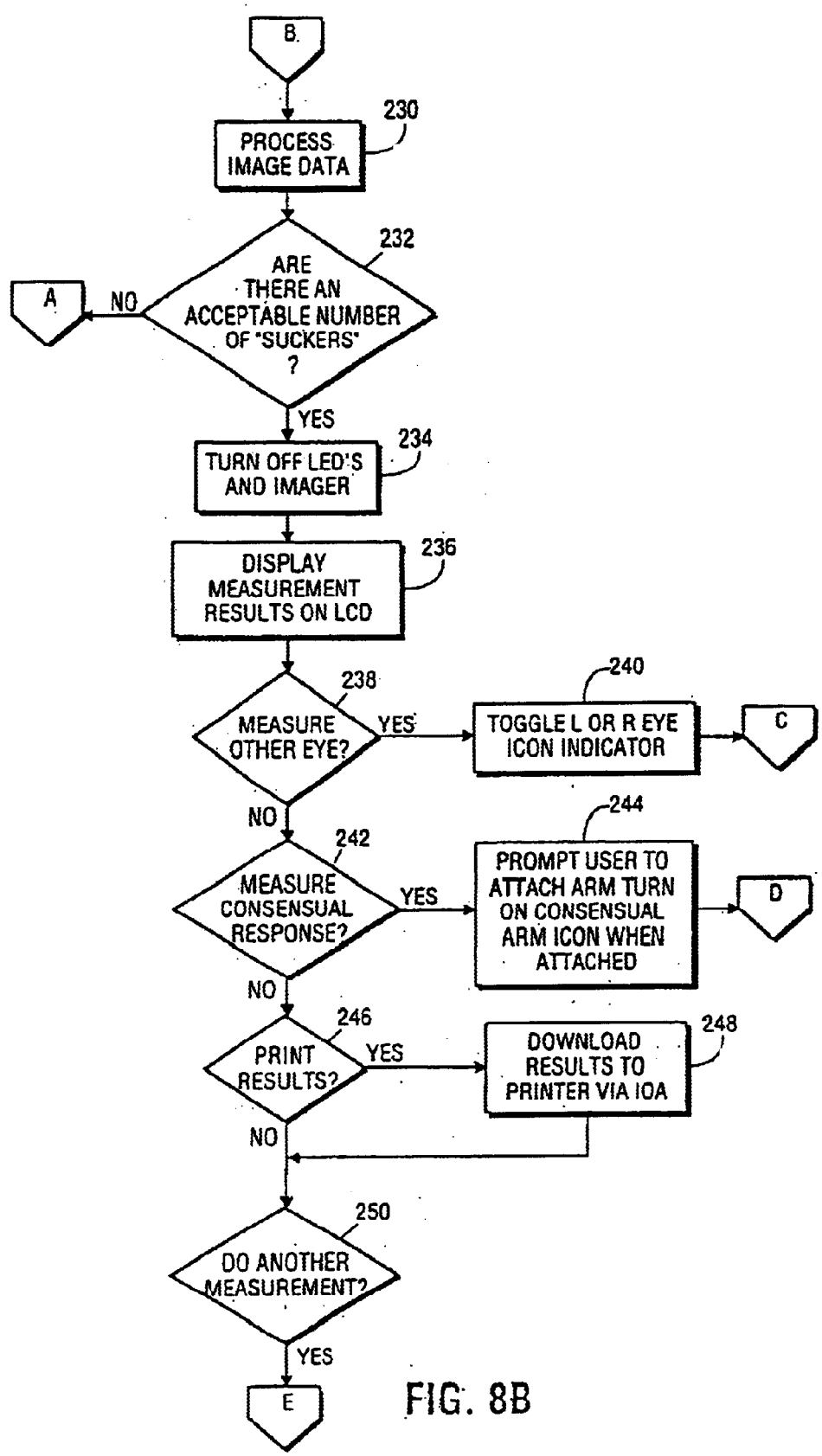

Turning now to FIG. 8, operation of a pupilometer 10 in accordance with the present invention proceeds as follows. Generally the pupilometer 10 will be configured according to a default mode of operation. The default mode defines a set of values for basic operation of the device. The defined values may include, for example, values for scan duration, illumination duration and/or profile, stimulus duration and/or profile and stimulus intensity level. However, it will be appreciated that all of the above-listed values may be programmably set under control of the graphic user interface object 100. Thus, it will be appreciated that default programming values generally will be utilized by the pupilometer 10 absent entry of an override by the user in a scan sequence program mode.

A typical image acquisition and analysis procedure may proceed as follows. If the pupilometer 10 has been idle for a predetermined period of time (e.g., 120 seconds), the pupilometer 10 is automatically placed in a battery-conserving sleep mode (step 202). By depressing the "scan" button 45 (shown in FIG. 2), the user causes the pupilometer 10 to enter a "ready" mode (step 200). At this time, the user is prompted to enter an alphanumeric subject or patient identification number via the keypad 39 or to download any necessary patient information from a network computer via an infrared data interface, such as an IRDA interface that is provided on numerous conventional personal computer products (step 204). Once any requisite patient identification data has been entered into the system, the user is prompted via the liquid crystal display 36 or an audio prompt to hold down the "scan" button 45 and to position the pupilometer 10 in front of the eye 38 of a subject (step 210).

When the user depresses the "scan" button 45, the microprocessor (not shown) initiates an imaging test sequence. The yellow LEDs 26 preferably are not activated during the test sequence. During the test sequence the images that are acquired by the imaging sensor 14 may be displayed on the liquid crystal display (LCD) 36. Preferably, the P-program analyzes the image data frames that are acquired during the test sequence, determines whether or not the pupilometer 10 is properly positioned for obtaining measurements, and determines if all necessary parameters are met to ensure high-quality data recovery. If the test criteria are not met, the user is prompted to reposition the pupilometer 10. After any requisite test criteria are met, the P-program will continue to run the test sequence until the "scan" button 45 is released.

Once the scan button 45 is released, the P-program preferably will initiate a prescribed measurement sequence and will activate the illumination system of the pupilometer 10 as needed during the measurement sequence. Upon completion of the measurement sequence, the user is informed via the LCD 36 or an audio prompt that the measurement sequence has been completed (steps 226–228).

Following completion of the measurement sequence, the P-program preferably will analyze the image data frames that have been obtained and will display the results of the analysis on the LCD 36. If the results are satisfactory (i.e., are statistically sound), the user may then be prompted to download the results to a printer or related network via the IrDA interface (not shown) (step 246). If the results are not satisfactory, the user is prompted to repeat the measurement sequence (step 222).

Finally, after an initial set of measurement are obtained, the user may be prompted for a decision to measure the pupilary characteristics of the other eye of the subject/patient, or the user may be prompted for a decision to make a consensual response measurement (steps 238, 242). The consensual response measurement may take the form of a "swinging flashlight" measurement discussed more fully below. If a consensual measurement is to be performed, the user may be prompted to couple a consensual measurement attachment (shown in FIG. 9) to the pupilometer and to position a yellow LED 52 mounted on the attachment in front of the appropriate eye of the subject/patient. If the consensual measurement attachment is permanently affixed to the pupilometer 10, the user may only need to deploy and/or properly position the attachment.

D. Incorporation of Consensual Measurement Apparatus in a Pupilometer in Accordance with the Present Invention The following description of incorporated consensual measurement apparatus applies to pupilometers 10, 300, and 400, but will only be described in connection with pupilometer 10 for convenience and brevity. It should be understood, however, that each of pupilometers 10, 300, and 400 are hand-held devices having similar dimensions, and the consensual measurement apparatus described herein can be used with each of them.

Figure 9:
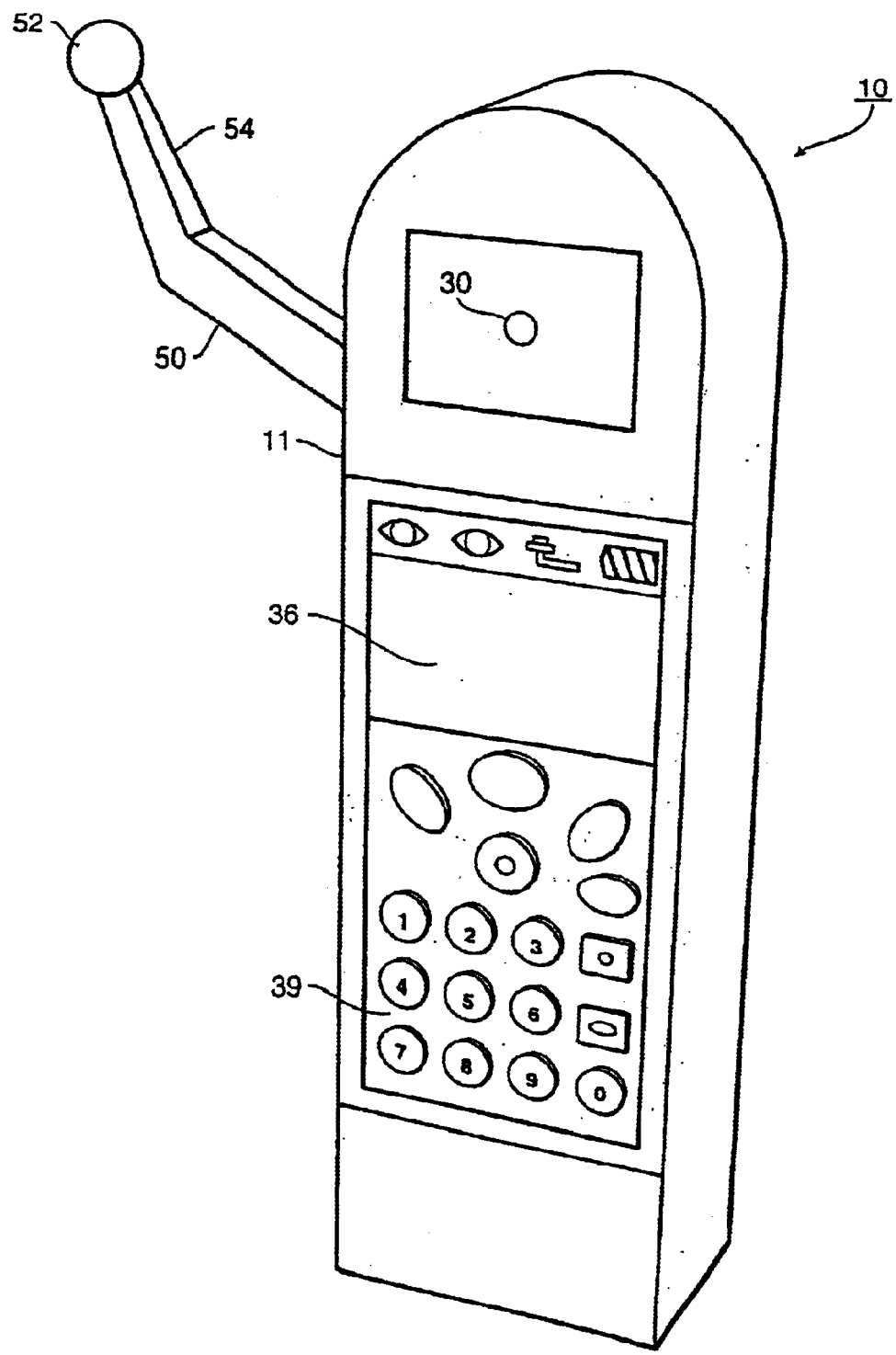
FIG. 9 is an illustration of a pupilometer incorporating a consensual measurement attachment in accordance with the present invention.

Turning now to FIG. 9, a pupilometer 10 in accordance with the present invention may incorporate a consensual measurement apparatus or armature 50 to enable consensual pupilary 10 responses to be analyzed. In a preferred embodiment, the armature 50 may detachably engage a main body 11 of the pupilometer 10. However, as explained above, the armature 50 also may be permanently affixed to the main body 11 of the pupilometer 10.

One test for analyzing consensual pupilary responses is commonly referred to within the medical community as a "swinging flashlight test." During a typical swinging flashlight test one eye of a subject is monitored, and a visible light stimulus is applied first to the eye of the patient that is being monitored, then to the eye of the patient that is not monitored and, finally, again to the eye that is monitored. If the eyes of the patient are normal, the pupil of the monitored eye should constrict in response to all of the light stimulus pulses (regardless of which eye the stimulus pulse is applied to). Following application of the first light stimulus, the pupil of the monitored eye should begin to dilate, and upon application of the second light stimulus (i.e., upon application of stimulus to the non-monitored eye), the pupil of the monitored eye should again constrict. If the monitored pupil does not respond adequately to the second stimulus pulse, it may be inferred that the retina of the non-monitored eye somehow may be impaired. If the monitored pupil does not respond adequately to the third stimulus pulse, it may be inferred that the retina of the monitored eye somehow may be impaired.

By using a consensual measurement attachment 50 in accordance with the present invention, it is possible to perform a "swinging flashlight" test using the pupilometer 10. For example, when performing a "swinging flashlight" test, the P-program may first cause the yellow LEDs 26 within the pupilometer 10 to be activated for a period of, for example, 1 second. The P-program then may deactivate the yellow LEDs 26, and 0.5 second following deactivation of the yellow LEDs 26 may activate for 0.5 second the yellow LED 52 located at the distal end 54 of the consensual attachment. Finally, after deactivating the yellow LED 52 and waiting for a period of, for example, 0.5 second, the P-program may again activate the yellow LEDs 26 for a period of 1 second. Image frames may be obtained by the imaging sensor 14 at a rate of, for example, 10 frames per second and for a total period of 5.0 or more seconds to evaluate the consensual response of the imaged eye. If desired, the process may be repeated a predetermined number of times.

E. Miscellaneous System Calibration and Pupil Identification Processing Techniques The following system calibration and pupil identification processing techniques are applicable to pupilometers 10, 300, and 400, but will only be described in connection with pupilometer 10 for convenience and brevity. It should be understood, however, that just as with the above description of the software, the techniques described now can be used with pupilometers 300 and 400 as well.

In alternative embodiments, the P-program of a pupilometer 10 in accordance with the present invention may incorporate a calibration algorithm that uses acquired data descriptive of the perimeter of the iris 37 of the eye 38 of a patient to define a relationship between pixel spacing data and real world measurement parameters and/or to evaluate an orientation of a patient's eye 38 in relation to the pupilometer 10.

For example, in one innovative aspect, the P-program of a pupilometer 10 may cause the iris of the eye of a patient to be illuminated by blue light (i.e., may activate the blue LED 28) and, while the patient's eye is so illuminated, may obtain an image of the sclera/iris border of the patient's eye. A flying spot or similar processing algorithm may then be used to identify a best fitting elliptical circumference for the sclera/iris border of the patient's eye, and the radii or horizontal and vertical diameters of the circumference may be compared to or correlated with assumed sclera/iris border radii or diameters to provide a correlation between a pixel count and a real world measurement. For example, if the horizontal diameter of a sclera/iris border is assumed to be 11.7 mm, and the sclera/iris border measures 117 pixels in diameter, the P-program of the pupilometer 10 may derive a pixel measurement to real world correlation factor of 10 pixels/mm, and that correlation factor may be used to provide the user with pupil measurement information. In accordance with one preferred form of the present invention, the horizontal diameter of the sclera/iris border is assumed to be 11.75 mm for in all subjects. However, those skilled in the art will appreciate that a different diameter, such as 11.0 mm or 12.0 mm, may also be assumed.

Similarly, by evaluating the shape of the sclera/iris border of an eye it is possible to estimate the angular orientation of the eye with respect to the pupilometer 10 and, moreover, to evaluate the orientation of an eye with relation to a vertical axis of the eye. Preferably, this may be done by evaluating a degree of ellipticity of the imaged sclera/iris border and assuming that the shape of the sclera/iris border has a predetermined elliptical shape. Such, measurements may be further refined by comparing the shape of a pupil to the shape of a surrounding sclera/iris border to determine whether variations in the shape of a pupil arise from angular orientation of the eye in relation to the pupilometer 10, or from non-uniformities or irregularities in the perimeter of the pupil.

In another innovative aspect, a pupilometer 10 in accordance with the present invention may include software for utilizing physical landmarks to assist in locating a pupil within an image data frame. In such an embodiment, the feature extraction object 106 of the P-program executed by the microprocessor (not shown) may include code for identifying characteristic structures of ocular tissue such as eyelids and/or eyelashes within an image data frame, and for using the location of those structures to predict the location of a pupil within the image data frame. Additional landmarks that may be located in accordance with the present invention include the lachrymal punctum, lachrymal caruncula, and lateral and medial papebral commisures of a patient's eye. These landmarks also may be used to identify which eye of a patient is being monitored.

F. Diagnostics Systems and Methods in Accordance with the Present Invention

In still another innovative aspect, the present invention is directed to improved diagnostics systems and methods incorporating a pupilometer 10 and medical database (not shown). For example, it is contemplated in accordance with the present invention that data representative of a plurality of pupilary response or configuration characteristics associated with one or more physical or pathological conditions may be stored within a medical diagnostics data base, that a pupilometer 10 may be used to obtain data descriptive of one or more pupilary response or configuration characteristics from a patient, and that the obtained data may be compared to the stored data within a data analysis system to identify one or more physiologic or pathologic characteristics or conditions of the patient. Further, in a preferred form, the obtained and/or stored pupil configuration data may be descriptive of one or more static or dynamic regional non-uniformities that may exist within the perimeter of a patient's pupil.

Figure 11:
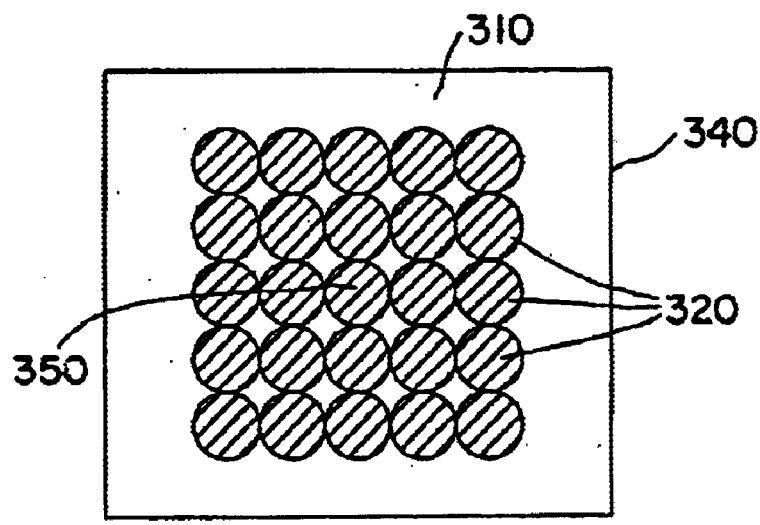
FIG. 11 is a front view of the diode array depicted in FIG. 10.
Figure 12:
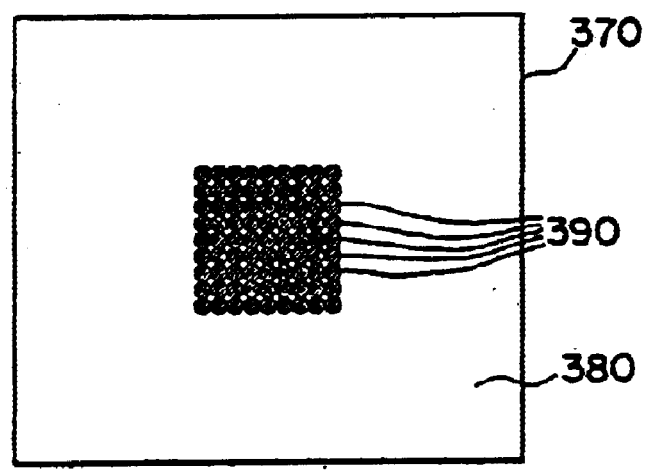
FIG. 12 is a front view of a diode array in accordance with another embodiment of the present invention.

One example is a medical diagnostics system, as shown in FIG. 10, wherein the pupilometer 300 can be used to screen for Glaucoma. The pupilometer 300 can comprise a diode array 340 having a diffuse yellow light emitting surface 310 in conjunction with series N concentrated (optically) blue LEDS 320 which are imaged onto the retina of an eye in such a way as to illuminate N specific regions. A single on-axis red LED 350 can also be used as a fixation target to assure consistent retinal stimulus. The diode array 340 is also shown in FIG. 11 in a two-dimensional frontal or overhead view.

Sensitivity and accuracy of Glaucoma detection are improved by this system and method, which employs the diffuse yellow light emitting surface 310 in order to bias the background as yellow and the N concentrated blue LEDS 320 as flicker sources for stimulating the retina of the eye. Alternatively, the background light can be white while the source of flicker light can generate green light. Again, the IR LEDS are activated to illuminate the eye and enable the imaging sensor to detect pupillary response to the stimulatory light, i.e., the blue or green light.

The microprocessor 34, as shown in FIG. 1, controls the operation and function of this illumination system as previously described. The subject patient's point-of-gaze is verified for each measurement utilizing the tracking features of pupilometer 10. The pupilary response for each of N blue (or green) illumination regions is documented and compared to a database of normal measurements to determine if the response falls out of range. Alternatively, the pupilary response for each of N blue (or green) illumination regions can be compared to a database of measurements that indicate Glaucoma to determine whether they fall within those measurements and therefore indicate Glaucoma. Both amplitude and velocity of pupilary response is detected by the imaging sensor 14 and recorded by the image signal processing board 34. It is expected that in the presence of Glaucoma peripheral retinal response to blue (or green) light stimulus will be compromised.

The pupilometer 10 can also be used to diagnose elevated intracranial pressure. Under conditions of elevated ICP, the profusion of the occulomotor nerve (CNIII) is compromised, therefore affecting the propagation properties of action potentials through nerve fibers. Therefore, under amplitude modulated conditions, which elicit maximal pupilary response, the dynamic properties of the light-reflex as a function of time will deteriorate to a greater extent in those individuals with elevated levels of intracranial pressure. The stimulus/illumination object 102 can be amplitude modulated, and either or both the blue LEDS 28 and the yellow LEDS 26 can act as the stimulus source and can be amplitude modulated also. In this embodiment, the stimulus/illumination object 102 can control the amplitude of the stimulus source to repeatedly cycle the pupil reflex. The pupilometer 10 can be used to capture a sequence of images of the eye while a continuous and amplitude modulated light stimulus is applied to the eye, either by the blue LEDS 28 or the yellow LEDS 26. The P-program software detects the pupil margin and calculates the average rate of change of the pupil as a response to an extended duration amplitude modulated light stimulus source. The average rate of change data is then compared to normative or previously recorded data for the patient or a normal subject as an indicator of abnormality and CNIII involvement due to elevated intracranial pressure.

When the amplitude of the light projected to the eye is increased, the constriction velocity of the pupil should increase. But, the constriction velocity for each successive increase in light stimulus amplitude is generally lower in those individuals who are diagnosed with elevated intracranial pressure. On the other hand, as the amplitude is decreased, dilation velocity in individuals with intracranial pressure increases at a more rapid pace. Thus, constriction and dilation velocity, as well as pupilary amplitude, can be used to determine whether an individual has elevated levels of intracranial pressure.

The pupilometer 10 can also be used to diagnose impairment to brain function. The task of fixating on a target and maintaining this fixation as the target is moved about the visual field requires constant cortical feedback and cerebellar eye movement correction. The ability to visually track a moving target can be assessed by tracking actual point-of-gaze and comparing this information to a stored expected value for a set pattern of target movement. Substantial deviation from the expected value is an indication of brain disorder. Alternatively, the stored expected value can represent brain function impairment rather than representing a normal brain with no brain function impairment. In this case, values that fall within the range of the stored expected value represent brain function impairment. In addition, simultaneous presentation of multiple target points in the visual field has a predictable effect on paint of gaze for normally functioning brains even at a young age. Deviation from the predicted behavior to multiple point targets may give rise to the early diagnosis of Autism.

The system for diagnosing impairment to brain function comprises a pupilometer, such as the pupilometer 300 shown in FIG. 10, a moveable target or light source, a database for storing data descriptive of one or more pupilary characteristics associated with a set pattern of target movement, and a central processing unit coupled to the pupilometer. The target may be on the pupilometer itself, and may be comprised of a light generated by a visible light source, or any other visible object. For example, the pupilometer 300 may have a diode array such as the diode array 370 shown in FIG. 13, which is similar to the diode array 340 used for glaucoma detection. The main difference between the two diode arrays is that the diode array 370 has more LEDS fixed onto a yellow light emitting surface 380 defining a surface area the same or similar in size to the surface area of light emitting surface 310 of diode array 340. Individual elements or LEDS 390 of the diode array 370 can be sequentially turned on and the subjects pupillary movement analyzed according to the subjects ability to track the apparent motion of the LEDS.

The point-of-gaze is determined by detecting features of the eye in addition to the pupil and using fiducial alignment references generated by the system. The P-program will generate a frame by frame history of the point-of-gaze and compare the test results to a figure-of-merit for a normal brain given the same set of visual stimuli. Ultimately the system will indicate the type of tracking error that occurred (i.e., degree of overshoot, magnitude of lag, static dwell time) each of which indicate specific brain disorders.

The pupilometer 10 of FIG. 1 or the pupilometer 400 of FIG. 13 can also be used to test the functional integrity of afferent peripheral and cranial pathways as well as testing efferent cranial nerve involvement in patients with afferent pupilary defects. The pupil is mediated by a complex control system for which the output (pupil size) is determined by the sum of various autonomic inputs. The autonomic inputs that affect the pupil include both sympathetic and parasympathetic constituents. Noxious stimulation such as a pin-prick, sudden exposure to hot or cold, electrical current or pinching should result in a pupilary response. The response may include pupilary amplitude response to pain, reflexive point-of-gaze eye-movement or reflexive blinking.

In the pupilometer testing system described herein, the pupil is observed under a constant background light condition, such as IR light from IR LEDS 24 (or 424 on pupilometer 400), or yellow light from yellow LEDS 26 of the pupilometer 10. Meanwhile, noxious stimulation from a noxious stimulus source 17 is presented to the subject patient, and this stimulation is controlled with precise timing by the pupilometer's microprocessor 34 (or 434 on pupilometer 400), which is in electrical communication with the noxious stimulus source 17 through auxiliary connector 15 (or 415 on pupilometer 400). The magnitude, direction of gaze and temporal characteristics of the eye response including blinking are determined by image processing means in the P-program software. Sources of noxious stimuli, which are controlled by the pupilometer without exposing the patient to tissue damaging effects, include brief pulses of air, release of small bursts of cryogenic spray, such as Halocarbon 134$a$, and small electrical currents. These stimuli are applied to various dermatopic areas in addition to afferent-sensory areas such as the tympanic membrane and the cornea, which are innervated by cranial nerves.

The noxious stimuli are generated by a noxious stimulus source 17 connected to the pupilometer 10 by auxiliary connector 15 (or auxiliary connector 415 on pupilometer 400). For dorsal root and spinal cord involvement a small canister of compressed $CO_2$ gas with an electronically controlled regulation valve is electrically coupled to the auxiliary connector or output port 15 on the pupilometer 10 (or 415 on pupilometer 400). The valve releases a metered volume of $CO_2$ gas providing a source of extreme cold which can be directed to any dermatome area. The pupil is evaluated for the pain/cold response at progressively lower dermatopic areas until a differential in pupilary response is detected. The P-program software calculates/detects the pupil margin and calculates the gross rate of change of the pupil as a response to the noxious stimulus.

The corneal-blink reflex, which is mediated by afferents of the ophthalmic branch of the trigeminal nerve (CNV) can be tested by the system using compressed air or a fan which produces a small puff of air on the cornea while the P-program monitors pupil as well as eyelid response.

The eye moves away from an ice water stimulus on the tympanic membrane in the ear. A cryogenic spray can produce the same behavior via noxious stimulus to the ear. A $CO_2$ canister and regulated valve as described earlier and electrically coupled to the pupilometer 10 or the pupilometer 400, is used to measure the eye movement in response to this tympanic membrane stimulation.

Finally, the pupilometer 10 or the pupilometer 400 can also be used in connection with a system for testing the functional integrity of auditory pathways (vestibulocochlear nerve and the auditory cortex) by detecting pupilary response to sound stimulus. In this implementation of a pupilometer-based hearing testing system, the pupil is observed under a constant background light condition while an audible stimulus is presented to the subject or patient.

This stimulus is controlled with precise timing, amplitude and frequency by the pupilometer's microprocessor 34 (or 340 on pupilometer 400). The amplitude and temporal (i.e., velocity) characteristics of the pupilary response are detected by the imaging sensor 14 (or 414 on pupilometer 400) and recorded by the microprocessor 34 (or 434 on pupilometer 400).

This aspect of the invention can also be implemented by a system comprising a pupilometer as described herein, a sound generating transducer capable of generating sound in various amplitudes and frequencies and in electrical communication with one or more ear-pieces or speakers 19, as shown in FIGS. 1 and 13, a database for storing data descriptive of one or more pupilary characteristics associated with a set pattern of sound stimuli, and a central processing unit. The data stored in the database can represent pupilary responses that are normal and indicative of healthy auditory pathways, or can represent pupilary responses that represent abnormal or disfunctional auditory pathways. In either case, a comparison of the data representing the patient's or subject's pupilary response to the data stored in the database, using the central processing unit, can determine the functional integrity of the patient's auditory pathways.

While the invention is susceptible to various modifications and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

What is claimed is:

1. A pupilometer comprising:
    a visible light source for generating light to stimulate a retina of an eye;
    an IR light source for generating IR light for illuminating a pupil of the eye;
    an imaging sensor for generating signals representative of the pupil of the eye;
    a microprocessor; and
    a program executable by said microprocessor for enabling said microprocessor to process signals received from said imaging sensor and to thereby identify the pupil's dynamic response to the visible light generated by the visible light source.
2. The pupilometer of claim 1, wherein the visible light source generates green light.
3. The pupilometer of claim 1, wherein the visible light source generates blue light.
4. The pupilometer of claim 1, wherein the signal received from the imaging sensor represents the amplitude of the pupil's response to the light generated from the visible light source.
5. The pupilometer of claim 1, wherein the signal received from the imaging sensor represents the velocity of the pupil's response to the light generated from the visible light source.
6. The pupilometer of claim 1, wherein the light generated from the visible light source is projected onto at least one region of the retina of the eye.
7. The pupilometer of claim 6, wherein the light generated from the visible light source is projected onto multiple regions on the retina of the eye in succession.
8. The pupilometer of claim 1, wherein the microprocessor is electrically coupled to the visible light source, and wherein the program enables said microprocessor to cause a plurality of light stimulus pulses to be generated by said visible light source, and enables said imaging device to acquire a plurality of images of said pupil.
9. The pupilometer of claim 1, wherein the signal received from the imaging sensor represents the latency of pupilary response to the light generated from the visible light source.
10. The pupilometer of claim 1, wherein the signal received from the imaging sensor represents the constriction velocity of the pupil in response to the light generated from the visible light source.
11. The pupilometer of claim 1, wherein the signal received from the imaging sensor represents a first dilation velocity of the pupil.
12. The pupilometer of claim 1, wherein the signal received from the imaging sensor represents a second dilation velocity of the pupil.
13. The pupilometer of claim 1, wherein the signal received from the imaging sensor represents a maximum diameter of the pupil.
14. The pupilometer of claim 1, wherein the signal received from the imaging sensor represents a minimum diameter of the pupil.
15. The pupilometer of claim 1, wherein the visible light source generates white light.
16. The pupilometer of claim 1, wherein the visible light source generates yellow diffuse light.
17. A method for detecting glaucoma comprising the steps of:
    providing a pupilometer;
    obtaining, using the pupilometer, pupilary response data from an eye of a patient, said pupilary response data being representative of one or more pupilary response characteristics of said eye;
    storing within a database data representative of a plurality of pupilary response characteristics;
    comparing within an automated data analysis system said pupilary response data obtained from said patient with said data representative of a plurality of pupilary response characteristics to determine whether the patient's pupilary response data indicates Glaucoma.
18. The method of claim 17, wherein the pupilometer comprises a visible light source, an IR light source, an imaging sensor, a microprocessor, and a program executable by said microprocessor.

19. The method of claim 18, wherein the step of obtaining the patient's pupilary response data comprises the steps of:
   illuminating the eye the IR light from the IR light source;
   projecting a first image of the eye to the imaging sensor; and
   transmitting data representative of the first image of the eye to the microprocessor.

20. The method of claim 19 further comprising the steps of:
   projecting light from the visible light source onto a retina of the eye;
   projecting a second image of the eye to the imaging sensor; and
   transmitting data representative of the second image of the eye to the microprocessor.

21. The method of claim 17, wherein the data representative of a plurality of pupilary response characteristics is associated with Glaucoma.

22. The method of claim 17, wherein the data representative of a plurality of pupilary response characteristics is associated with a healthy eye.

23. The method of claim 17, wherein the pupilary response characteristics of said eye comprise the velocity of pupilary response to retinal stimulation by light.

24. The method of claim 17, wherein the pupilary response characteristics of said eye comprise the amplitude of pupilary response to retinal stimulation by light.

25. The method of claim 17, wherein the database is in electrical communication with the pupilometer.

26. The method of claim 17, wherein the data analysis system is in electrical communication with the pupilometer.

27. A system for use in diagnosing glaucoma, said system comprising:
   a pupilometer for obtaining data descriptive of one or more pupilary characteristics from an eye of a patient;
   a database for storing data descriptive of a plurality of pupilary characteristics; and a central processing unit coupled to said pupilometer and said database for comparing said data obtained by said pupilometer to said data stored within said database such that Glaucoma may be diagnosed based upon said comparison.

28. The system of claim 27, wherein the pupilometer comprises a first visible light source, a second visible light source, an IR light source, and an imaging sensor.

29. The system of claim 28, wherein the first visible light source generates white light.

30. The system of claim 28, wherein the first visible light source generates a yellow diffuse light.

31. The system of claim 28, wherein the second visible light source generates green light.

32. The system of claim 28, wherein the second visible light source generates blue light.

33. The system of claim 27 further comprising a display coupled to said central processing unit for displaying images of said patient's pupil and for providing an indication of whether or not said pupilary characteristics of said patient correspond to any of said pupilary characteristics represented by said data stored within said database.

34. A system for use in diagnosing impairment to brain function, said system comprising:
   a pupilometer for obtaining data descriptive of one or more pupilary characteristics from a subject;
   a movable target;
   a database for storing data descriptive of one or more pupilary characteristics associated with a set pattern of target movement; and
   a central processing unit coupled to the pupilometer and the database for comparing the data obtained by the pupilometer to the data stored within the database to assess the subject's level of brain function.

35. The system of claim 34, wherein the pupilometer comprises a visible light source, and the movable target comprises light generated by said visible light source.

36. The system of claim 35 further comprising a second movable target.

37. A method for diagnosing impairment to brain function comprising the steps of:
   providing a pupilometer;
   providing a movable target in the visual field of a subject;
   moving the target within the visual field of the subject in a set pattern of target movement;
   obtaining, using the pupilometer, a first set of data descriptive of one or more pupilary characteristics from an eye of the subject as the subject follows the target;
   storing within a database a second set of data descriptive of plurality of pupilary characteristics associated with the set pattern of target movement;
   comparing within a data analysis system said first set of data with said second set of data to determine whether the subject's brain function is impaired.

38. The method of claim 31 further comprising the step of providing a second moveable target in the visual field of the subject.

39. The method of claim 37, wherein the second set of data is associated with impairment to brain function.

40. The method of claim 37, wherein the second set of data is associated with normal levels of brain function.

41. The method of claim 37, wherein the database is in electrical communication with the pupilometer.

42. The method of claim 37, wherein the data analysis system is in electrical communication with the pupilometer.

43. A system for diagnosing neurological disease or trauma, said system comprising:
   a pupilometer for obtaining data descriptive of one or more pupilary characteristics from an eye of a patient;
   a stimulus source in communication with the pupilometer; and
   a central processing unit coupled to the pupilometer and in communication with the stimulus source, said central processing unit being capable of activating the stimulus source thereby sending a stimulus to an anatomical structure of the patient.

44. The system of claim 43, wherein the stimulus source is a noxious stimulus source.

45. The system of claim 44, wherein the stimulus source is a container of a liquid substance.

46. The system of claim 45, wherein the stimulus source is a container of compressed liquid substance.

47. The system of claim 43, further comprising:
   a database for storing a second set of data descriptive of a plurality of pupilary characteristics, said central processing unit in communication with the database;
   and a data analysis system, said data analysis system capable of comparing the first set of data and second set of data such that neurological disease or trauma may be diagnosed based on such comparison.

48. The system of claim 43, wherein the stimulus source is configured to provide an electrical current.

49. The system of claim 43, wherein the stimulus source is a light source.

50. The system of claim 43, wherein the central processing unit is capable of synchronizing the activation of the stimulus source with the pupilometer.

51. The system of claim 43, wherein the data comprises pupilary latency indicia.

52. The system of claim 43, wherein the data comprises pupilary constriction velocity indicia.

53. The system of claim 43, wherein the data comprises pupilary first and second dilation velocity indicia.

54. The system of claim 43, wherein the data comprises pupilary amplitude indicia.

55. The system of claim 43, wherein the data comprises pupilary diameter indicia.

56. The system of claim 43, wherein the data comprises segmental dynamic analysis indicia.

57. The system of claim 43, wherein the data comprises segmental static analysis indicia.

58. The system of claim 43, wherein the central processing unit comprises an algorithm configured to convert said data to one or more scalar values.

59. A method for diagnosing neurological disease or trauma, said method comprising the steps of:
providing a pupilometer comprising a central processing unit and a memory;
providing a stimulus source, said stimulus source in communication with the pupilometer;
activating the stimulus source with the pupilometer thereby causing the stimulus source to send a stimulus to an anatomical structure of a patient;
obtaining, using the pupilometer, temporal data with respect to the activation of the stimulus source; and
obtaining, using the pupilometer, a first set of data descriptive of one or more pupilary characteristics from an eye of the patient.

60. The method of claim 59, wherein the pupilometer comprises a light source.

61. The method of claim 59, wherein the pupilary response characteristics of the eye comprise pupilary constriction velocity indicia.

62. The method of claim 59, wherein the pupilary response characteristics of the eye comprise pupilary amplitude indicia.

63. The method of claim 59, wherein the anatomical structure that is stimulated with the stimulus comprises the cornea.

64. The method of claim 59, wherein the anatomical structure that is stimulated with the stimulus comprises the ear.

65. The method of claim 59, wherein the anatomical structure that is stimulated comprises dermatopic areas.

66. The method of claim 59, wherein the database is in electrical communication with the pupilometer.

67. The method of claim 59, wherein the data analysis system is in electrical communication with the pupilometer.

68. The method of claim 59, further comprising the steps of:
storing within a database a second set of data descriptive of a plurality of pupilary characteristics associated with pupilary response to a stimulus; and
comparing within a data analysis system said first set of data with said second set of data to determine whether neurological disease or trauma in the patient is indicated.

69. The method of claim 59, wherein the stimulus source is a noxious stimulus source.

70. The method of claim 59, wherein the stimulus source is a light source.

71. The method of claim 59, wherein the step of activating the stimulus source is controlled and synchronized by the central processing unit.

72. The method of claim 59, wherein the stimulus source is configured to provide an electrical current.

73. The method of claim 59, further comprising the step of obtaining, using the pupilometer, a second set of data descriptive of one or more pupilary characteristics from a second eye of the patient.

74. The method of claim 73, further comprising the step of comparing within a data analysis system said first set of data with said second set of data.

75. The method of claim 73, further comprising the step of converting, using an algorithm, said second set of data to one or more scalar values.

76. The method of claim 73, further comprising the step of converting, using an algorithm, said first and said second sets of data to one or more scalar values.

77. The method of claim 59, wherein the first set of data comprises pupilary latency indicia.

78. The method of claim 59, wherein the first set of data comprises pupilary constriction velocity indicia.

79. The method of claim 59, wherein the first set of data comprises pupilary first and second dilation velocity indicia.

80. The method of claim 59, wherein the first set of data comprises pupilary amplitude indicia.

81. The method of claim 59, wherein the first set of data comprises pupilary diameter indicia.

82. The method of claim 59, wherein the first set of data comprises segmental dynamic analysis indicia.

83. The method of claim 59, wherein the first set of data comprises segmental static analysis indicia.

84. The method of claim 59, further comprising the step of converting, using an algorithm, said first set of data to one or more scalar values.

85. The method of claims 84, 75, or 76 further comprising the step of applying said scalar values to a scale indicative of a state of neurological health.

86. The method of claim 59, wherein the anatomical structure that is stimulated with the stimulus comprises one or more from the following group: skin, muscle, or peripheral nerve.

87. A system for testing the functional integrity of a patient's auditory pathways, said system comprising:
a pupilometer for obtaining data descriptive of one or more pupilary characteristics of the patient;
a sound generating transducer; and
a central processing unit in communication with the pupilometer and sound generating transducer, said central processing unit capable of activating and controlling the sound generating transducer and synchronizing the pupilometer with the sound generating transducer.

88. The system of claim 87, wherein the sound generating transducer is capable of generating sound in more than one amplitude and more than one frequency.

89. The system of claim 87, wherein the central, processing unit is capable of storing temporal data relating to the activation of the sound generating transducer.

90. The system of claim 87, wherein the central processing unit is capable of controlling temporal data relating to the activation of the sound generating transducer.

91. The system of claim 87, further comprising a database for storing data descriptive of one or more pupilary characteristics associated with a set pattern of sound stimuli, wherein the central processing unit is further capable of comparing the data obtained by the pupilometer to the data stored with the database to asses the functional integrity of the patient's auditory pathways based on said comparison.

92. The system of claim 87, further comprising one or more ear-pieces in communication with the sound generating transducer.

93. The system of claim 87, wherein the data comprises pupilary latency indicia.

94. The system of claim 87, wherein the data comprises pupilary constriction velocity indicia.

95. The system of claim 87, wherein the data comprises pupilary first and second dilation velocity indicia.

96. The system of claim 87, wherein the data comprises pupilary amplitude indicia.

97. The system of claim 87, wherein the data comprises pupilary diameter indicia.

98. The system of claim 87, wherein the data comprises segmental dynamic analysis indicia.

99. The system of claim 87, wherein the data comprises segmental static analysis indicia.

100. The system of claim 87, wherein the central processing unit comprises an algorithm configured to convert said data to one or more scalar values.

101. A method for testing the functional integrity of a patient's auditory pathways, said method comprising the steps of:
providing a pupilometer;
providing a central processing unit in communication with the pupilometer;
providing a sound generating transducer capable of transmitting an auditory stimulus, said sound generating transducer in communication with the central processing unit, wherein the central processing unit is capable of activating and controlling the sound generating transducer;
using the pupilometer, activating the transducer to produce a sound; and
obtaining, using the pupilometer, a first set of data descriptive of one or more pupilary characteristics from an eye of the patient.

102. The method of claim 101, wherein the pupilometer comprises a light source.

103. The method of claim 101, wherein the pupilometer is in electrical communication with the sound generating transducer.

104. The method of claim 101, wherein the transducer is capable of generating sound in more than one amplitude and more than one frequency.

105. The method of claim 101, wherein the transducer and pupilometer are synchronized.

106. The method of claim 101, wherein the response characteristics of the eye comprises the velocity of pupilary response to auditory stimulus generated by the transducer.

107. The method of claim 101, wherein the response characteristics of the eye comprises the amplitude of pupilary response to auditory stimulus generated by the transducer.

108. The method of claim 101, further comprising the steps of:
storing within a database a second set of data descriptive of one or more pupilary characteristics associated with a set pattern of sound stimuli; and
comparing within a data analysis system said first set of data with said second set of data to assess the functional integrity of the patient's auditory pathways based upon said comparison.

109. The method of claim 108, wherein the database is in electrical communication with the pupilometer.

110. The method of claim 108, wherein the data analysis system is in electrical communication with the pupilometer.

111. The method of claim 101, further comprising the steps of:
providing one or more ear-pieces in electrical communication with the transducer; and
inserting the one or more ear-pieces into one or both ears of the patient.

112. The method of claim 101, further comprising the step of obtaining, using the pupilometer, a second set of data descriptive of one or more pupilary characteristics from a second eye of the patient.

113. The method of claim 112, further comprising the step of comparing within a data analysis system said first set of data with said second set of data.

114. The method of claim 112, further comprising the step of converting, using an algorithm, said second set of data to one or more scalar values.

115. The method of claim 112, further comprising the step of converting, using an algorithm, said first and said second sets of data to one or more scalar values.

116. The method of claim 101, wherein the first set of data comprises pupilary latency indicia.

117. The method of claim 101, wherein the first set of data comprises pupilary constriction velocity indicia.

118. The method of claim 101, wherein the first set of data comprises pupilary first and second dilation velocity indicia.

119. The method of claim 101, wherein the first set of data comprises pupilary amplitude indicia.

120. The method of claim 101, wherein the first set of data comprises pupilary diameter indicia.

121. The method of claim 101, wherein the first set of data comprises segmental dynamic analysis indicia.

122. The method of claim 101, wherein the first set of data comprises segmental static analysis indicia.

123. The method of claim 101, further comprising the step of converting, using an algorithm, said first set of data to one or more scalar values.

124. The method of claims 123, 114 or 115, further comprising the step of applying said scalar values to a scale indicative of a state of auditory pathway health.

125. A method for diagnosing a medical condition, said method comprising the steps of:
providing a pupilometer;
providing a central processing unit in communication with the pupilometer;
providing an amplitude modulated light source for generating light, said light source in communication with the central processing unit, wherein the central processing unit is capable of activating and controlling the amplitude modulated light source;
continuously projecting the light for a given length of time onto the eye of a patient in a predetermined pattern of amplitude modulation; and
obtaining, using the pupilometer, a first set of data representative of a pupil's response to the modulated light.

126. The method of claim 125, further comprising the steps of:
storing within a database a second set of data representing pupilary response to light stimulus received in said predetermined pattern of amplitude modulation; and
comparing within a data analysis system said first set of data with said second set of data in order to detect neurological deterioration.

127. The method of claim 126, wherein the database is in electrical communication with the pupilometer.

128. The method of claim 126, wherein the data analysis system is in electrical communication with the pupilometer.

129. The method of claim 126, wherein the second set of data represents data taken from one or more healthy individuals.

130. The method of claim 126, wherein the second set of data represents data taken from one or more individuals with neurological deterioration.

131. The method of claim 126, wherein the first and second sets of data are both taken from the same individual.

132. The method of claim 125, wherein the pupilometer is in electrical communication with the light source.

133. The method of claim 125, further comprising the step of obtaining, using the pupilometer, a second set of data descriptive of one or more pupilary characteristics from a second eye of the patient.

134. The method of claim 133, further comprising the step of comparing within a data analysis system said first set of data with said second set of data.

135. The method of claim 133, further comprising the step of converting, using an algorithm, said second set of data to one or more scalar values.

136. The method of claim 133, further comprising the step of converting, using an algorithm, said first and said second sets of data to one or more scalar values.

137. The method of claim 125, wherein the first set of data comprises pupilary latency indicia.

138. The method of claim 125, wherein the first set of data comprises pupilary constriction velocity indicia.

139. The method of claim 125, wherein the first set of data comprises pupilary first and second dilation velocity indicia.

140. The method of claim 125, wherein the first of data comprises pupilary amplitude indicia.

141. The method of claim 125, wherein the first set of data comprises pupilary diameter indicia.

142. The method of claim 125, wherein the first set of data comprises segmental dynamic analysis indicia.

143. The method of claim 125, wherein the first set of data comprises segmental static analysis indicia.

144. The method of claim 125, further comprising the step of converting, using an algorithm, said first set of data to one or more scalar values.

145. The method of claims 144, 135, and 136, further comprising the step of applying said scalar values to a scale indicative of a medical condition.

146. A method for correlating a pupilary response with pathological indications, said method comprising the steps of:
    storing within a database data representative of a plurality of pupilary response characteristics associated with one or more pathological indications;
    using a pupilometer, obtaining pupilary response data from a patient, said pupilary response data being representative of one or more pupilary response characteristics of said patient;
    providing a data analysis system comprising a microprocessor, said microprocessor in communication with the database and the pupilometer; and
    comparing within said data analysis system said pupilary response data obtained from said patient with said data representative of a plurality of pupilary response characteristics to identify one or more pathological indications of said patient.

147. The method of claim 146, wherein the database and data analysis system are integrated into the pupilometer.

148. The method of claim 146, wherein the pupilary response data comprises pupilary latency indicia.

149. The method of claim 146, wherein the pupilary response data comprises pupilary constriction velocity indicia.

150. The method of claim 146, wherein the pupilary response data comprises pupilary first and second dilation velocity indicia.

151. The method of claim 146, wherein the pupilary response data comprises pupilary amplitude indicia.

152. The method claim 146, wherein the pupilary response data comprises pupilary diameter indicia.

153. The method of claim 146, wherein the pupilary response data comprises segmental dynamic analysis indicia.

154. The method of claim 146, wherein the first set of data comprises segmental static analysis indicia.

155. A method for correlating pupilary measurements with pathological indications, said method comprising the steps of:
    storing within a database data representative of a plurality of pupilary data and associated pathological indications;
    using a pupilometer, obtaining pupilary data from a patient;
    providing a data analysis system comprising a microprocessor, said microprocessor in communication with the database and the pupilometer; and
    comparing with said data analysis system said pupilary data obtained from said patient with said data from said database to identify one or more pathological indications of said patient.

156. The method of claim 155, wherein both the data from the database and the data obtained from the patient represent pupilary shape or pupilary dynamics data.

157. The method of claim 156, wherein both the data from the database and the data obtained from the patient comprise data descriptive of a pupilary response to at least one visible light stimulus pulse.

158. The method of claim 156, wherein both the data from the database and the data obtained from the patient comprise data descriptive of a pupilary change in shape responsive to at least one light stimulus pulse.

159. The method of claim 156, wherein both the data from the database and the data obtained from the patient comprise data descriptive of a pupilary response to ambient light exposure.

160. The method of claim 156, wherein both the data from the database and the data obtained from the patient comprise pupilary latency indicia.

161. The method of claim 156, wherein both the data from the database and the data obtained from the patient comprise pupilary constriction velocity indicia.

162. The method of claim 156, wherein both the data from the database and the data obtained from the patient comprise pupilary first and second dilation velocity indicia.

163. The method of claim 156, wherein both the data from the database and the data obtained from the patient comprise pupilary amplitude indicia.

164. The method of claim 156, wherein both the data from the database and the data obtained from the patient comprise pupilary diameter indicia.

165. The method of claim 156, wherein both the data from the database and the data obtained form the patient comprise segmental dynamic analysis indicia.

166. The method of claim 156, wherein both the data from the database and the data obtained from the patient comprise segmental static analysis indicia.

167. The method of claim 155, wherein the database and data analysis system are integrated into the pupilometer.

168. A method for assessing a state of health of an individual or physiological system of said individual, said method comprising the steps of:
- using a pupilometer, obtaining pupilary response data from a patient, said pupilary response data being representative of one or more pupilary response characteristics of said patient;
- providing a data analysis system comprising a microprocessor, said microprocessor in communication with the pupilometer; and
- using the data analysis system to derive a scalar value based on the pupilary response data from the patient.

169. The method of claim 168, further comprising the step of applying the scalar value to a scale indicative of a state of health of an individual or a physiological system of an individual.

170. The method of claim 168, wherein the step of applying the scalar value to a scale is performed by the data analysis system.

171. The method of claim 168, wherein the database and data analysis system are integrated into the pupilometer.

172. A system for use in diagnosing pathological conditions, said system comprising:
- a pupilometer for obtaining a first set of data descriptive of one or more pupilary characteristics from a patient;
- a database for storing a second set of data descriptive of a plurality of pupilary characteristics and associated physical conditions; and
- a central processing unit in communication with said pupilometer and said database for comparing said first set of data with said second set of data such that a pathological condition of said patient may be diagnosed based on said comparison.

173. The system of claim 172, wherein the first and second sets of data comprise image data.

174. The system of claim 172, wherein the first and second sets of data comprise alphanumeric values.

175. The system of claim 172 further comprising a processing subroutine for generating a scalar indicator based upon a result of said comparison of the first and second sets of data by the central processing unit.

176. The system of claim 172 further comprising a display coupled to said central processing unit for displaying images of said patient's pupil and for providing an indication of whether or not said pupilary characteristics of said patient correspond to any of said pupilary characteristics represented by said second set of data.

177. The system of claim 172, wherein the database and central processing unit are integrated into the pupilometer.

178. A pupilometer comprising:
- a display, an imaging device and a microprocessor, said microprocessor being coupled to said display, and said imaging device, said microprocessor comprising a memory, wherein said memory has stored therein a program comprising:
  - image acquisition code for enabling said microprocessor to cause said imaging device to acquire a plurality of images of a first pupil of an individual's eye;
  - image analysis code for enabling said microprocessor to process data sets representative of said images of said pupil to obtain information descriptive of said pupil; and
  - display code for enabling said microprocessor to cause said information to be depicted on said display.

179. The pupilometer of claim 178, further comprising a first visible light source, and an IR light source, wherein said microprocessor is in communication with said first visible light source and said IR light source, and said program further comprises:
- stimulus control code for enabling said microprocessor to cause said visible light source to generate a first visible light stimulus pulse for illuminating a first eye; and
- illumination control code for enabling said microprocessor cause said IR light source to generate IR light for illuminating a pupil of said first eye during a duration of said first visible light stimulus pulse.

180. The pupilometer of claim 179, further comprising an armature extending laterally from a main body of the pupilometer, said armature comprising a second visible light source, said microprocessor in communication with said second visible light source, wherein the stimulus control code is capable of enabling the microprocessor to cause said second visible light source to generate a second visible light stimulus pulse for illuminating a second eye of the individual at a predetermined time following termination of said first visible light stimulus pulse, and to cause said first visible light source to generate a third visible light stimulus pulse for illuminating said first eye at a predetermined time following termination of said second visible light stimulus pulse.

181. The pupilometer of claim 180, wherein the microprocessor is capable of storing and controlling the times at which the microprocessor activates the first visible light source and a time at which the microprocessor activates the second visible light source.

182. The pupilometer of claim 181, wherein the microprocessor is capable of synchronizing the activation of the first and second visible light sources.

183. A medical diagnosis system comprising:
- a pupilometer for obtaining data descriptive of one or more eye movement characteristics from a subject;
- a movable target;
- a database for storing data descriptive of one or more eye movement characteristics associated with a set pattern of target movement; and
- a central processing unit coupled to the pupilometer and the database for comparing the data obtained by the pupilometer to the data stored with the database to assess the subject's level of brain function.

184. The system of claim 183, wherein the pupilometer comprises a visible light source, and the movable target comprises light generated by said visible light source.

185. The system of claim 184 further comprising a second movable target.

186. A method for diagnosing a medical condition, said method comprising the steps of:
- providing a pupilometer;
- providing a movable target in the visual field of a subject;
- moving the target with the visual field of the subject in a set pattern of target movement;
- obtaining, using the pupilometer, a first set of data descriptive of one or more eye movement characteristics from an eye of the subject as the subject follows the target;
- storing within a database a second set of data descriptive of a plurality of eye movement characteristics associated with the set pattern of target movement;
- comparing within a data analysis system said first set of data with said second set of data to determine whether the subject's brain function is impaired.

187. The method of claim 186 further comprising the step of providing a second moveable target in the visual field of the subject.

188. The method of claim 186, wherein the second set of data is associated with impairment to brain function.

189. The method of claim 186, wherein the second set of data is associated with normal levels of brain function.

190. The method of claim 186, wherein the database is in electrical communication with the pupilometer.

191. The method of claim 186, wherein the data analysis system is in electrical communication with the pupilometer.

192. A method for examining an individual comprising the steps of:

provinding a pupilometer comprising an imaging sensor, a data processor, and a program executable by said data processor for analyzing pupilary response to stimuli;

using the pupilometer to acquire a first set of data representative of a response of a first eye of the patient to a first stimulus;

using the pupilometer to acquire of second set of data representative of a response of a second eye of the patient to a second stimulus, the second stimulus being applied at a predetermined time following termination of the first stimulus; and using the pupilometer to correlate the first set of data with the second set of data to derive a value.

193. The method of claim 192, further comprising the step of comparing the value with a value corresponding with a set of normal responses to the stimulus.

194. The method of claim 192, further comprising the step of comparing the value with a value corresponding with a set of abnormal responses to the stimulus.

195. The method of claim 192, wherein the value derived is a scalar value, said method further comprising the step of applying the scalar value to scale.

196. The method of claim 192, wherein the pupilometer comprises a stimulus source, and the first and second stimuli are delivered by the pupilometer.

197. The method of claim 196, wherein the pupilometer comprises an armature that extends from a main body of the pupilometer for supporting a second stimulus source, and the first stimulus is delivered by the first stimulus source, and the second stimulus is delivered by the second stimulus source.

* * * * *

UNITED STATES PATENT AND TRADEMARK OFFICE
CERTIFICATE OF CORRECTION

| | | |
|---|---|---|
| PATENT NO. | : 6,820,979 B1 | |
| DATED | : November 23, 2004 | |
| INVENTOR(S) | : Lawrence W. Stark et al. | |

It is certified that error appears in the above-identified patent and that said Letters Patent is hereby corrected as shown below:

Column 23, line 60 thru Column 24, line 5,
Delete text beginning with "1. A pupilometer comprising:" to "visible light source."

Column 24,
Line 5, insert the following claim:

1. A pupilometer comprising:
      a visible light source for generating light to stimulate a retina of an eye;
      an IR light source for generating IR light for illuminating a pupil of the eye
      an imaging sensor for generating signals representative of the pupil of the eye;
      a microprocessor; and
      a program for sequencing said light source executable by said microprocessor for enabling said microprocessor to process signals received from said imaging sensor and to thereby identify the pupil's dynamic response to the visible light generated by the visible light source.

Column 26,
Line 29, the numeral "31" should read -- 37 --.
Lines 40-51, delete the text beginning with "43. A system for diagnosing" to "structure of the patient."
Line 51, insert the following claim:

43. A system for diagnosing neurological disease or trauma, said system comprising:
      a pupilometer for obtaining data descriptive of one or more pupilary characteristics from an eye of a patient;
      a stimulus source in communication with the pupilometer;
      a central processing unit for sequencing said stimulus source coupled to the pupilometer and in communication with the stimulus source, said central processing unit being capable of activating the stimulus source thereby sending a stimulus to an anatomical structure of the patient.

Column 27,
Lines 22-36, delete the text beginning with "59. A method for diagnosing" to "an eye of the patient."
Line 36, insert the following claim:

59. A method for diagnosing neurological disease or trauma, said method comprising the steps of:
      providing a pupilometer comprising a central processing unit and a memory;
      providing a stimulus source, said stimulus source in communication with the pupilometer;
      sequentially activating the stimulus source with the pupilometer thereby causing the stimulus source to send a stimulus to an anatomical structure of a patient;
      obtaining, using the pupilometer, temporal data with respect to the activation of the stimulus source; and
      obtaining, using the pupilometer, a first set of data descriptive of one or more pupilary characteristics from an eye of the patient.

Column 33,
Line 19, the numeral "168" should read -- 169 --.

UNITED STATES PATENT AND TRADEMARK OFFICE
CERTIFICATE OF CORRECTION

PATENT NO. : 6,820,979 B1
DATED : November 23, 2004
INVENTOR(S) : Lawrence W. Stark et al.

It is certified that error appears in the above-identified patent and that said Letters Patent is hereby corrected as shown below:

Column 34,
Line 10 before the word "cause" insert -- to --.

Signed and Sealed this

Eighteenth Day of January, 2005

JON W. DUDAS
*Director of the United States Patent and Trademark Office*